(12) United States Patent
Gontcharov et al.

(10) Patent No.: US 7,714,130 B2
(45) Date of Patent: May 11, 2010

(54) PROCESSES FOR PREPARING GONADOTROPIN RELEASING HORMONE RECEPTOR ANTAGONISTS

(75) Inventors: Alexander V. Gontcharov, Rivervale, NJ (US); Gulnaz Khafizova, West Nyack, NY (US); John R. Potoski, West Nyack, NY (US); Donna Mary Huryn, Monmouth, NJ (US)

(73) Assignee: Wyeth, Madison, NJ (US)

( * ) Notice: Subject to any disclaimer, the term of this patent is extended or adjusted under 35 U.S.C. 154(b) by 873 days.

(21) Appl. No.: 11/154,921

(22) Filed: Jun. 16, 2005

(65) Prior Publication Data

US 2005/0282820 A1  Dec. 22, 2005

Related U.S. Application Data

(60) Provisional application No. 60/580,665, filed on Jun. 17, 2004.

(51) Int. Cl.
  *C07D 413/00*  (2006.01)
  *C07D 417/00*  (2006.01)
  *C07D 419/00*  (2006.01)
(52) U.S. Cl. ..................................................... 544/368
(58) Field of Classification Search ........................ None
See application file for complete search history.

(56) References Cited

U.S. PATENT DOCUMENTS

| | | | |
|---|---|---|---|
| 3,325,506 A | 6/1967 | Jones et al. | |
| 3,996,233 A | 12/1976 | Denzel et al. | |
| 4,459,296 A | 7/1984 | Ancher et al. | |
| 4,833,142 A | 5/1989 | Hartog et al. | |
| 5,057,517 A | 10/1991 | Johnston et al. | |
| 5,338,740 A | 8/1994 | Carpino et al. | |
| 5,424,313 A | 6/1995 | Hartog et al. | |
| 5,502,187 A | 3/1996 | Ayer et al. | |
| 5,576,460 A | 11/1996 | Buchwald et al. | |
| 5,643,944 A | 7/1997 | Garfield et al. | |
| 5,716,964 A | 2/1998 | Hansen, Jr. et al. | |
| 6,277,989 B1 | 8/2001 | Chakravarty et al. | |
| 6,306,859 B1 | 10/2001 | Childers et al. | |
| 6,307,087 B1 | 10/2001 | Buchwald et al. | |
| 6,310,066 B1 | 10/2001 | Kelly et al. | |
| 6,313,126 B1 | 11/2001 | Mewshaw et al. | |
| 6,376,141 B1 | 4/2002 | Mishra et al. | |
| 6,399,629 B1 | 6/2002 | Chamberland et al. | |
| 6,476,031 B1 | 11/2002 | Chakravarty et al. | |
| 6,492,517 B1 | 12/2002 | Burdeniuc | |
| 6,548,505 B1 | 4/2003 | Martin et al. | |
| 6,559,167 B1 | 5/2003 | Garst et al. | |
| 6,620,529 B1 | 9/2003 | Ise et al. | |
| 6,696,469 B2 | 2/2004 | Peglion et al. | |
| 6,723,724 B2 | 4/2004 | Koh et al. | |
| 6,821,967 B2 | 11/2004 | Lehmann-Lintz et al. | |
| 6,841,549 B1 | 1/2005 | Asano et al. | |
| 2001/0020030 A1 | 9/2001 | Stewart et al. | |
| 2002/0013324 A1 | 1/2002 | Childers et al. | |
| 2002/0055133 A1 | 5/2002 | Hahn et al. | |
| 2002/0072053 A1 | 6/2002 | McNally et al. | |
| 2002/0147197 A1 | 10/2002 | Newman et al. | |
| 2002/0161010 A1 | 10/2002 | Chakravarty et al. | |
| 2002/0168630 A1 | 11/2002 | Fleming et al. | |
| 2002/0182623 A1 | 12/2002 | Lefevre et al. | |
| 2003/0021851 A1 | 1/2003 | Goswami et al. | |
| 2003/0028018 A1 | 2/2003 | Renhowe et al. | |
| 2003/0051260 A1 | 3/2003 | Chada et al. | |
| 2003/0055057 A1 | 3/2003 | Blume et al. | |
| 2003/0069248 A1 | 4/2003 | Chakravarty et al. | |
| 2003/0165920 A1 | 9/2003 | Chou et al. | |
| 2003/0220365 A1 | 11/2003 | Stewart et al. | |
| 2004/0018240 A1 | 1/2004 | Ohmachi et al. | |
| 2004/0036868 A1 | 2/2004 | Jones et al. | |
| 2004/0082635 A1 | 4/2004 | Hashimoto et al. | |
| 2004/0082798 A1 | 4/2004 | Alonso-Alija et al. | |
| 2004/0102502 A1 | 5/2004 | Watanabe et al. | |
| 2004/0121008 A1 | 6/2004 | Shiraishi et al. | |
| 2004/0122001 A1 | 6/2004 | Agejas-Chicharro et al. | |
| 2004/0219208 A1 | 11/2004 | Kawamura et al. | |
| 2005/0009894 A1 | 1/2005 | Babin et al. | |
| 2005/0065196 A1 | 3/2005 | Inaba et al. | |
| 2005/0101647 A1 | 5/2005 | Oda et al. | |
| 2005/0282820 A1 | 12/2005 | Gontcharov et al. | |

(Continued)

FOREIGN PATENT DOCUMENTS

DE           39 26 770 A1      2/1991

(Continued)

OTHER PUBLICATIONS

Artamonova, et al., "Preparation of 1,5-Disubstituted Tetrazoles Under Phase-Transfer Conditions", Synthesis (1996) 12, 1428-30.

(Continued)

*Primary Examiner*—James O Wilson
*Assistant Examiner*—Jeffrey H Murray
(74) *Attorney, Agent, or Firm*—Wilmer Cutler Pickering Hale and Dorr LLP

(57) ABSTRACT

Methods of making Gonadotropin Releasing Hormone ("GnRH") (also known as Leutinizing Hormone Releasing Hormone) receptor antagonists, comprising reacting a compound having Formula I:

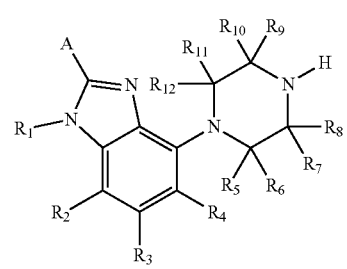

with a compound having formula $L_g-(CR_{13}R_{14})_k-D$, are disclosed.

51 Claims, No Drawings

U.S. PATENT DOCUMENTS

| | | |
|---|---|---|
| 2006/0019965 A1 | 1/2006 | Garrick et al. |
| 2006/0111355 A1 | 5/2006 | Garrick et al. |
| 2006/0189616 A1 | 8/2006 | Pelletier et al. |
| 2006/0189617 A1 | 8/2006 | Pelletier et al. |
| 2006/0189618 A1 | 8/2006 | Pelletier |
| 2006/0189619 A1 | 8/2006 | Tadayon et al. |
| 2006/0264631 A1 | 11/2006 | Green et al. |
| 2006/0270848 A1 | 11/2006 | Lundquist et al. |

FOREIGN PATENT DOCUMENTS

| | | |
|---|---|---|
| DE | 10030376 | 1/2002 |
| DE | 10110750 | 9/2002 |
| DE | 20217340 | 2/2003 |
| EP | 0 138 280 A | 4/1985 |
| EP | 0300726 | 1/1989 |
| EP | 0400974 | 12/1990 |
| EP | 0434038 | 6/1991 |
| EP | 0 471 236 B1 | 2/1992 |
| EP | 1136483 | 9/2001 |
| EP | 1197485 | 4/2002 |
| EP | 1239283 | 9/2002 |
| GB | 1009807 | 11/1965 |
| GB | 1049330 | 11/1966 |
| GB | 2 097 790 A | 11/1982 |
| GB | 2369616 | 6/2002 |
| GB | 2370270 | 6/2002 |
| IT | 01298727 | 2/2000 |
| JP | 2002161084 | 6/2002 |
| JP | 2002193946 | 7/2002 |
| JP | 2002212101 | 7/2002 |
| JP | 2003040890 | 2/2003 |
| JP | 2003083968 | 3/2003 |
| JP | 2003231687 | 8/2003 |
| NL | 6409237 | 4/1965 |
| NL | 6413475 | 5/1965 |
| RU | 2182708 | 5/2002 |
| WO | WO-9320078 | 10/1993 |
| WO | WO-9907703 | 2/1999 |
| WO | WO-9916755 | 4/1999 |
| WO | WO-9955672 | 11/1999 |
| WO | WO-9962908 | 12/1999 |
| WO | WO 00/02887 | 1/2000 |
| WO | WO-0002887 | 1/2000 |
| WO | WO-0012089 | 3/2000 |
| WO | WO-0040554 | 7/2000 |
| WO | WO 01/02369 A | 1/2001 |
| WO | WO-0147898 | 7/2001 |
| WO | WO-0149688 | 7/2001 |
| WO | WO-0157038 | 8/2001 |
| WO | WO-0170728 | 9/2001 |
| WO | WO-0170743 | 9/2001 |
| WO | WO-0174786 | 10/2001 |
| WO | WO-0208221 | 1/2002 |
| WO | WO-0208245 | 1/2002 |
| WO | WO-0214859 | 2/2002 |
| WO | WO 02/22600 | 3/2002 |
| WO | WO-0218383 | 3/2002 |
| WO | WO-0221135 | 3/2002 |
| WO | WO-0222598 | 3/2002 |
| WO | WO-0222600 | 3/2002 |
| WO | WO-0228839 | 4/2002 |
| WO | WO-0230935 | 4/2002 |
| WO | WO-0232422 | 4/2002 |
| WO | WO-0234263 | 5/2002 |
| WO | WO-0235474 | 5/2002 |
| WO | WO-0236562 | 5/2002 |
| WO | WO-0240019 A1 | 5/2002 |
| WO | WO-0240653 | 5/2002 |
| WO | WO-0241906 | 5/2002 |
| WO | WO-0242292 | 5/2002 |
| WO | WO-0243709 | 6/2002 |
| WO | WO-0244168 | 6/2002 |
| WO | WO-0244170 | 6/2002 |
| WO | WO-0245707 | 6/2002 |
| WO | WO-0248152 | 6/2002 |
| WO | WO-0250062 | 6/2002 |
| WO | WO-02051409 | 7/2002 |
| WO | WO-02055012 | 7/2002 |
| WO | WO-02055013 | 7/2002 |
| WO | WO-02059088 | 7/2002 |
| WO | WO-02062949 | 7/2002 |
| WO | WO-02064590 | 8/2002 |
| WO | WO-02068399 | 9/2002 |
| WO | WO-02069901 | 9/2002 |
| WO | WO-02071073 | 9/2002 |
| WO | WO-02072549 | 9/2002 |
| WO | WO-02074340 | 9/2002 |
| WO | WO-02083952 | 9/2002 |
| WO | WO-02076439 | 10/2002 |
| WO | WO-02076926 | 10/2002 |
| WO | WO-02076947 | 10/2002 |
| WO | WO-02076960 | 10/2002 |
| WO | WO-02076976 | 10/2002 |
| WO | WO-02079192 | 10/2002 |
| WO | WO-02079690 | 10/2002 |
| WO | WO-02081463 | 10/2002 |
| WO | WO-02083143 | 10/2002 |
| WO | WO-02083608 | 10/2002 |
| WO | WO-02089738 | 11/2002 |
| WO | WO-02101087 | 11/2002 |
| WO | WO-02102774 | 12/2002 |
| WO | WO-02102978 | 12/2002 |
| WO | WO-03004023 | 1/2003 |
| WO | WO-03004488 | 1/2003 |
| WO | WO-03007945 | 1/2003 |
| WO | WO-03013488 | 2/2003 |
| WO | WO-03013609 | 2/2003 |
| WO | WO-03018835 | 3/2003 |
| WO | WO-03021851 | 3/2003 |
| WO | WO-03022214 | 3/2003 |
| WO | WO-03024401 | 3/2003 |
| WO | WO-03025563 | 3/2003 |
| WO | WO-03026664 | 4/2003 |
| WO | WO-03026665 | 4/2003 |
| WO | WO-03026666 | 4/2003 |
| WO | WO-03027223 | 4/2003 |
| WO | WO-03031436 | 4/2003 |
| WO | WO-03032984 | 4/2003 |
| WO | WO-03035065 | 5/2003 |
| WO | WO-03035644 | 5/2003 |
| WO | WO-03037871 | 5/2003 |
| WO | WO-03037872 | 5/2003 |
| WO | WO-03038401 | 5/2003 |
| WO | WO-03048140 | 6/2003 |
| WO | WO-03053939 A1 | 7/2003 |
| WO | WO-03053948 | 7/2003 |
| WO | WO-03068754 | 8/2003 |
| WO | WO-03070943 | 8/2003 |
| WO | WO-03082272 | 10/2003 |
| WO | WO-03091408 | 11/2003 |
| WO | WO-03095432 | 11/2003 |
| WO | WO-03095995 | 11/2003 |
| WO | WO-2004016611 | 2/2004 |
| WO | WO 2004/035549 A | 4/2004 |

OTHER PUBLICATIONS

Dandegaonker, et al., "Brom-hydroxychalkone", *Monatshefte fuer Chemie* 96(2), (1965) 450-60.

Decroix, et al., "Synthese de Composes Polyazotes a Partir de Nitrile ou D'iminoether Furannique, Thiophenique et Selenophenique", *Bulletin de la Societe Chimique de France* (1976) (3-4, Pt. 2) 621-7.

Dox, "Acetamidine Hydrochloride", Org. Syntheses, Coll. vol. I, pp. 5-7.

Edlin, et al., "Selective Solvent Extraction of Tetrahedrally-Coordinating Transition Metal Ions From Acidic Aqueous Media Using Benzimidazole-Phosphinate Ligands: Specificity for Zinc(II) Over Copper(II)", New Journal of Chemistry 23(8) (1999) 819-26.

Gilchrist, et al., "Cyclisations of Ortho-Substituted N-Arylbenzimidoyl Nitrenes. Part 1. Cyclisations With Ortho-Alkyl Substituents: Skeletal Rearrangements and [1,9]Alkyl Migrations", J. Chem. Soc. Perkin Trans. I (1979) 1871-73.

Grenda, et al., "Novel Preparation of Benzimidazoles From N-Arylamidines. New Synthesis of Thiabendazole", J. Org. Chem. (1965) 30(1) 259-61.

Harris, et al., "Improved Functional Group Compatibility in the Palladium-Catalyzed Synthesis of Aryl Amines", Org. Lett. (2002) 4, 2885-8.

Haruki et al., "The Preparation of 2-Substituted Benzimidazoles and 2-Phenylnaphtho-[1, 2-d]imidazole From N-Arylamidines", Bull. Chem. Soc. Japan (1965) 38(10), 1805.

Haruki, et al., "Some Reactions of N-Haloamidines", Bull. Chem. Soc. Japan (1968) 41, 1361-67.

Hisano, et al., "Synthesis of Benzoxazoles, Benzothiazoles and Benzimidazoles and Evaluation of Their Antifungal, Insecticidal and Herbicidal Activities", Chem. Pharm. Bull. (1982) 30(8), 2996-3004.

Ichikawa, et al., "Acidic Properties of Benzimidazoles and Substituent Effects. IV. Relationship Between the Acidities of N'-(Substituted Phenyl) Arylamidines and Ring Closures to Imidazole", Chem. Pharm. Bull. (1979) 27(5), 1255-64.

Ichikawa, et al., "Acidic Properties of Benzimidazoles and Substituent Effects, III: The Substituent Effect on the Imidazole Cyclization From N-(m-Substituted-Phenyl) Picolylamidines", Organic Preparations and Procedures International (1979) 10(5), 205-9.

Katritzky, et al., "Pyrazolo(1,5-c)Pyrimidines From Pyrylium Salts And Amidrazones And Pyridine Imidoyl-N-Imides From Imidoyl Chlorides", Heterocycles (1982) 18, 21-28.

Liu, et al., "A Particularly Convenient Preparation of Benzohydroximinoyl Chlorides (Nitrile Oxide Precursors)", J. Org. Chem. (1980) 45, 3916-18.

López-Rodriguez, et al., "Pd(0) Amination of Benzimidazoles as an Efficient Method towards New (Benzimidazolyl) piperazines with High Affinity for the 5-HT$_{1A}$ Receptor", Tetrahedron 56 (2000) 3245-53.

López-Rodriguez, et al., "Synthesis of New (Benzimidazolyl) Piperazines with Affinity for the 5-HT$_{1A}$ Receptor Via Pd(0) Amination of Bromobenzimidazoles", Bioorg. & Med. Chem. Letters (1999) vol. 9, 2339-42.

Mewshaw, et al., "New Generation Dopaminergic Agents. 5. Heterocyclic Bioisosteres That Exploit The 3-OH-N$^1$-Phenylpiperazine Dopaminergic Template", Bioorg. & Med. Chem. Letters (1998) vol. 8, 2675-80.

Partridge, et al., "Cyclic Amidines. Part VII. Preparation of Benziminazoles From N'-Aryl-N-Hydroxyamidines", J. Chem. Soc. (1958) 2086-92.

Ramsden, et al., "Rearrangement and Cyclo-α-Elimination of N-Substituted Amidines Using (Diacetoxyiodo) Benzene", J. Chem. Soc. Perkin Trans. I (1995) 615-17.

Smith, et al., "The Thermal Breakdown of Diaryltetrazoles", J. Am. Chem. Soc. (1958) 80, 4647-54.

Smith, et al., "Amidrazones III. The Synthesis And Properties of 1,1,1-Trimethyl-2-(N-Phenlbenzimidoyl)Hydrazinium Hydroxide Inner Salt —A Novel Ylid", Tetrahedron Lett. (1973) 3941-42.

Wolfe, et al., "Simple, Efficient Catalyst System For The Palladium-Catalyzed Amination of Aryl Chlorides, Bromides, and Triflates", J. Org. Chem. (2000) 65, 1158-74.

Armer and Smelt, "Non_peptidic GnRh Receptor Antagonists," Current Medicinal Chemistry, vol. 11, pp. 3017-3028 (2004).

Barraclough et al. "Inotropic 'A' Ring Substituted Sulmazole and Isomazole Analogues," J. Med. Chem., 1999, 33, 2231-2239.

Buchwald, et al., "Long-term, Continuous Intravenous Heparin Administration by an Implantable Infusion Pump in Ambulatory Patients with Recurrent Venous Thrombosis", Surgery, 88(4):507-516 (1980).

Bundgaard, "Design and Application of Prodrugs", in *Textbook of Drug Design and Development,* Kgrogsgaard-Larsen, et al., eds., Harwood Academic Publishers, Chapter 5, pp. 113-191 (1991).

Chengalvala, M.V. et al., "GnRH Agonists and Antagonists in Cancer Therapy," Curr. Med. Chem.—Anti-Cancer Agents, 2003, 3, 399-410.

Clayton, et al., "Receptor-binding Affinity of Gonadotropin-releasing Hormone Analogs: Analysis by Radioligand-receptor Assay", Endocrinology, 106(4):1154-1159 (1980).

Controlled Drug Bioavailability, Drug Product Design and Performance, Smolen, et al., eds., John Wiley & Sons (1984).

*Design of Prodrugs,* Bundgaard, ed., Elsevier (1985).

Dorwald F.A., *Side Reactions in Organic Synthesis,* Wiley: VCH Weinheim, p. IX of Preface (2005).

Dox, A.W. "Acetamidine Hydrochloride," Organic Syntheses, 1932, pp. 5-7.

During, et al., "Controlled Release of Dopamine from a Polymeric Brain Implant: In Vivo Characterization", Ann. Neural., 25(4):351-356 (1989).

Enuguehard, et al., Ipso- or Cine-Substitutions of 6-Haloimidazo [1,2-a]pyridine Derivatives with Different Azoles Depending on the Reaction Conditions, J. Org. Chem, 68:5614-5617 (2003).

Finkelstein, "Regioselective Lithiation and Reaction of [1,2,4]Triazolo[1,5-a]pyridine and Pyrazolo[1,5-a]pyridine", J. Org. Chem., 57:5538-5540 (1992).

Goodson, "Dental Applications", Medical Applications of Controlled Release, vol. 2, Langer, et al,. eds., CRC Press, Boca Raton, FL, pp. 115-138 (1984).

Grundker, C. et al., "Gonadotropin-releasing hormone receptor-targeted gene therapy of gynecologic cancers," Molecular Cancer Therapeutics 2005; 4(2). Feb. 2005, 225-231.

Gudmundsson, et al., "Synthesis of Novel Imidazo[1,2-a]pyridines with Potent Activity Against Herpesviruses", Org. Lett, 5(8):1369-1372 (2003).

Hirsch, L. et al., "Birth Control: Birth Control Pill," TeensHealth, Nemours Foundation, http://kidshealth.org/teen/sexual_health/contraception/contraception_birth.html, Jul. 2, 2008.

Howard III, et al., "Intracerebral Drug Delivery in Rats with Lesion-Induced Memory Deficits", J. Neurosurg., 71:105-112 (1989).

Langer, "New Methods of Drug Delivery", Science, 249:1527-1533 (1990).

Langer, et al., "Chemical and Physical Structure of Polymers as Carriers for Controlled Release of Bioactive Agents: A Review", J. Macromol. Sci. Rev. Macromol. Chem., C23(1):61-126 (1983).

Levy, et al., "Inhibition of Calcification of Bioprosthetic Heart Valves by Local Controlled-Release Diphosphonate", Science, 228:190-192 (1985).

Lopez-Berestein, "Treatment of Systemic Fungal Infections with Liposomal-Amphotericin B", Liposomes in the Therapy of Infectious Diseases and Cancer, Lopez-Berstein, et al., eds., Alan R. Liss, Inc., New York, pp. 317-327 (1989).

López-Rodriguez, et al., "Design and Synthesis of New Benzimidazole-Arylpiperazine Derivatives Acting as Mixed 5-HT1A/5-HT3 Ligands", Bioorg. & Med. Chem. Letters (2003) vol. 13, 3177-80.

López-Rodriguez, et al., "Design and Synthesis of S-(-)-2-[[4-(napht-1-yl)piperazin-1-yl]-methyl]-1,4-dioxoperhydropyrrolo[1,2-a]pyrazine (CSP-2503) Using Computational Simulation. A 5-HT1A Receptor Agonist", Bioorg. & Med. Chem. Letters (2003) vol. 13, 1429-32.

March, Advanced Organic Chemistry: Reactions, Mechanisms and Structures, Fourth Edition, John Wiley & Sons, pp. 69-74 (1992).

Medical Applications of Controlled Release, vols. I and II, Langer and Wise, eds., CRC Press, Inc., Boca Raton, FL (1984).

*Methods in Enzymology,* vol. 112, Widder, et al., eds., Academic Press (1985).

Nielsen, et al., "Glycolamide Esters as Biolabile Prodrugs of Carboxylic Acid Agents: Synthesis, Stability, Bioconversion, and Physiochemical Properties", Journal of Pharmaceutical Sciences, 77(4):285-298 (1988).

Prodrugs as Novel Drug Delivery Systems, Higuchi, et al., eds., American Chemical Society, Washington, DC (1975).

Radebaugh, et al., "Preformulation", Remington: The Science and Practice of Pharmacy, 19th Edition, Gennaro, Ed., pp. 1447-1462 (1995).

Saudek, et al., "A Prelminiary Trial of the Programmable Implantable Medication System for Insulin Delivery", New England Journal of Med., 321(9):574-579 (1989).

Sefton, "Implantable Pumps", CRC Crit. Ref. Biomed. Eng., 14(3):201-240 (1987).

Treat, et al., "Liposome Encapsulated Doxorubicin Preliminary Results of Phase I and Phase ll Trials", Liposomes in the Therapy of Infectious Diseases and Cancer, Lopez-Berestein, et al., eds., Alan R. Liss, Inc., New York, pp. 353-365 (1989).

PROCESSES FOR PREPARING GONADOTROPIN RELEASING HORMONE RECEPTOR ANTAGONISTS

This application claims the benefit of provisional application U.S. Ser. No. 60/580,665, filed Jun. 17, 2004, which is hereby incorporated by reference into the subject application in its entirety.

Throughout this application, various publications are referenced. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure, as it appears in the U.S. Patent and Trademark Office patent file or records, but otherwise reserves any and all copyright rights whatsoever.

FIELD OF INVENTION

The present invention relates to processes for preparing Gonadotropin Releasing Hormone ("GnRH") (also known as Leutinizing Hormone Releasing Hormone ("LHRH")) receptor antagonists.

BACKGROUND

GnRH is a decameric peptide released from the hypothalamus. In the anterior pituitary gland, GnRH activates the GnRH receptor. Activation of the GnRH receptor triggers the release of follicle stimulating hormone (FSH) and leuteinizing hormone (LH). FSH and LH stimulate the biosynthesis and release of sex steroids in the gonads of both genders.

Typically, this is desirable, but certain sex hormone dependent pathological conditions exist where it would be beneficial to prevent activation of the GnRH receptor. For example, inhibition of the GnRH receptor can lead to a large drop in sex steroid production, which in turn can alleviate sex hormone dependent pathological conditions such as prostate cancer, endometriosis, uterine fibroids, uterine cancer, breast cancer, ovarian cancer, testicular cancer, or primary hirsutism. Moreover, there are other situations where it would be beneficial to prevent activation of the GnRH receptor, such as during some points of the in vitro fertilization process, such as to prevent LH surge.

Currently marketed GnRH therapeutics are peptides that exhibit receptor antagonism in one of two ways. The first is through GnRH receptor superagonism. The GnRH receptor, when stimulated in bursts, causes normal release of the gonadotropins, FSH and LH. Under constant stimulation, the receptor becomes desensitized and the overall effect is GnRH receptor inhibition. The superagonism process is somewhat undesirable, as inhibition via this process can take up to two weeks to arise in human patients. During this delay there is often an increase in disease symptoms due to the initial hormone stimulation phase. This phenomenon is referred to as flare.

The second method for receptor inhibition is through direct antagonism of the GnRH receptor with peptide antagonists. This causes an immediate drop in plasma LH levels. However, as mentioned above, current pharmaceuticals that cause blockade of the GnRH receptor are all peptides. As such they are not orally bioavailable and must be administered via parenteral means such as intravenous, subcutaneous or intramuscular injection. Thus, an orally effective GnRH antagonist would be of significant benefit.

Therefore, based upon the foregoing, it is clear that GnRH receptor antagonists are useful, and development of new GnRH receptor antagonists is highly desirable. U.S. Patent Application Ser. No. 60/580,640, the disclosure of which is incorporated herein as if reproduced in its entirety, teaches compounds of formula II and IV as defined herein useful as GnRH receptor antagonists.

However, it is desirable to have methods of making such compounds which are efficient for large scale production.

SUMMARY

The present invention provides methods comprising reacting compounds having Formula I:

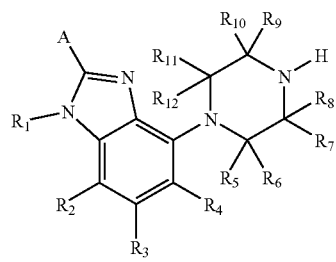

I wherein:
A is aryl or heteroaryl, each optionally substituted;
$R_1$, $R_2$, $R_3$, and $R_4$ are, independently, H or optionally substituted alkyl; and
$R_5$, $R_6$, $R_7$, $R_8$, $R_9$, $R_{10}$, $R_{11}$, and $R_{12}$, are, independently, H, alkyl, alkenyl, or alkynyl, each alkyl, alkenyl, or alkynyl being optionally substituted;

with compounds having formula:

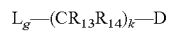

wherein:
D is H, alkyl, cycloalkyl, heterocycloalkyl, aryl, or heteroaryl, each alkyl, cycloalkyl, heterocycloalkyl, aryl, or heteroaryl being optionally substituted;
$L_g$ is halogen or $OSO_2R_{32}$, wherein $R_{32}$ is alkyl, aryl, or fluoroalkyl, each optionally substituted;
k is 0, 1, 2, or 3; and
$R_{13}$ and $R_{14}$ are, independently at each occurrence, H or optionally substituted alkyl, in an organic solvent in the presence of base, thereby forming compounds having Formula II, or a pharmaceutically acceptable salt thereof:

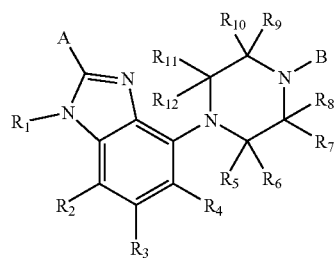

II wherein B is $(CR_{13}R_{14})_k$—D.

The present invention further comprises methods comprising reacting compounds having Formula III:

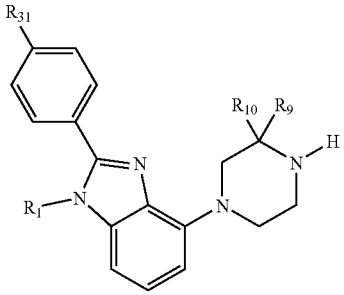

wherein:

R$_1$ is H or alkyl;

R$_9$ and R$_{10}$, are, independently, H, alkyl, alkenyl, or alkynyl, each alkyl, alkenyl, or alkynyl being optionally substituted; and R$_{31}$ is C$_1$-C$_6$ alkyl, C$_2$-C$_6$ alkenyl, C$_2$-C$_6$ alkynyl, NR$_{22}$R$_{23}$, CR$_{24}$(CF$_3$)$_2$, JR$_{22}$, or C(=O)R$_{22}$, wherein J is O or SO$_m$, wherein m is 0, 1, or 2;

R$_{22}$ and R$_{23}$ are, independently, H, C$_1$-C$_7$ alkyl, C$_2$-C$_7$ alkenyl, C$_2$-C$_7$ alkynyl, aryl, or heteroalkyl, each alkyl, alkenyl, alkynyl, aryl, or heteroalkyl being optionally substituted, alternatively, R$_{22}$ and R$_{23}$, taken together with the atoms to which they are attached, form a cyclic or heterocyclic group, e.g., of 3-8 ring members and the heteroatoms are selected from O, N and S, optionally substituted with R$_{20}$—E—R$_{21}$, wherein E is O, N, NR$_{21}$, or SO$_m$, R$_{20}$ and R$_2$, are, independently, H, C$_1$-C$_3$ alkyl, or heteroalkyl, alternatively, R$_{20}$ and R$_{21}$, taken together with the atoms to which they are attached, form a cyclic or heterocyclic group, e.g., of 3-8 ring members and the heteroatoms are selected from O, N and S; and R$_{24}$ is H, or OH;

with compounds having formula:

wherein:

D is heterocycloalkyl or heteroaryl, each optionally substituted;

L$_g$ is halogen or OSO$_2$R$_{32}$, wherein R$_{32}$ is alkyl, aryl, or fluoroalkyl, each optionally substituted;

k is 0, 1, 2, or 3; and

R$_{13}$ and R$_{14}$ are, independently at each occurrence, H or optionally substituted alkyl, in an organic solvent in the presence of base, thereby forming compounds having Formula IV, or a pharmaceutically acceptable salt thereof:

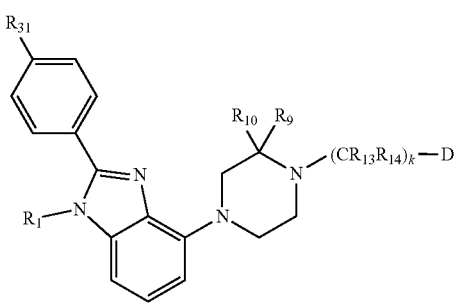

The present invention further comprises compounds having Formula III:

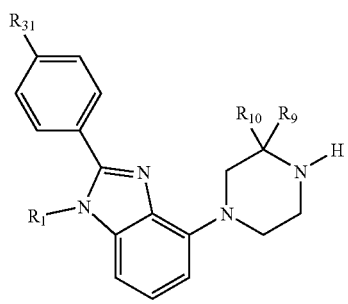

wherein:

R$_1$ is H or alkyl;

R$_9$ and R$_{10}$, are, independently, H, alkyl, alkenyl, or alkynyl, each alkyl, alkenyl, or alkynyl being optionally substituted; and R$_{31}$ is C$_1$-C$_6$ alkyl, C$_2$-C$_6$ alkenyl, C$_2$-C$_6$ alkynyl, NR$_{22}$R$_{23}$, CR$_{24}$(CF$_3$)$_2$, JR$_{22}$, or C(=O)R$_{22}$, wherein J is O or SO$_m$, wherein m is 0, 1, or 2;

R$_{22}$ and R$_{23}$ are, independently, H, C$_1$-C$_7$ alkyl, C$_2$-C$_7$ alkenyl, C$_2$-C$_7$ alkynyl, aryl, or heteroalkyl, each alkyl, alkenyl, alkynyl, aryl, or heteroalkyl being optionally substituted, alternatively, R$_{22}$ and R$_{23}$, taken together with the atoms to which they are attached, form a cyclic or heterocyclic group, e.g., of 3-8 ring members and the heteroatoms are selected from O, N and S, optionally substituted with R$_{20}$—E—R$_{21}$, wherein E is O, N, NR$_{21}$, or SO$_m$, R$_{20}$ and R$_2$, are, independently, H, C$_1$-C$_3$ alkyl, or heteroalkyl, alternatively, R$_{20}$ and R$_{21}$, taken together with the atoms to which they are attached, form a cyclic or heterocyclic group, e.g., of 3-8 ring members and the heteroatoms are selected from O, N and S; and R$_{24}$ is H, or OH.

DETAILED DESCRIPTION

In one embodiment, the present invention comprises a method comprising reacting a compound having Formula I:

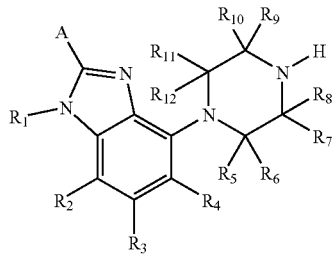

wherein:

A is aryl or heteroaryl, each optionally substituted;

R$_1$, R$_2$, R$_3$, and R$_4$ are, independently, H or optionally substituted alkyl; and R$_5$, R$_6$, R$_7$, R$_8$, R$_9$, R$_{10}$, R$_{11}$, and R$_{12}$, are, independently, H, alkyl, alkenyl, or alkynyl, each alkyl, alkenyl, or alkynyl being optionally substituted;

with a compound having formula:

wherein:

D is H, alkyl, cycloalkyl, heterocycloalkyl, aryl, or heteroaryl, each alkyl, cycloalkyl, heterocycloalkyl, aryl, or heteroaryl being optionally substituted;

$L_g$ is halogen or $OSO_2R_{32}$, wherein $R_{32}$ is alkyl, aryl, or fluoroalkyl, each optionally substituted;

k is 0, 1, 2, or 3; and $R_{13}$ and $R_{14}$ are, independently at each occurrence, H or optionally substituted alkyl, in an organic solvent in the presence of base, thereby forming a compound having Formula II, or salts thereof:

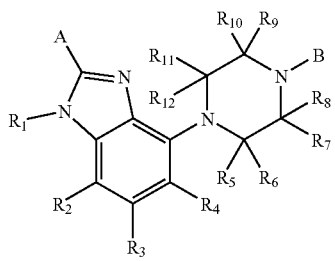

wherein B is $(CR_{13}R_{14})_k$—D.

In one embodiment, D is optionally substituted heteroaryl. In another embodiment, D is optionally substituted $C_1$-$C_6$ alkyl.

In one embodiment, $R_1$, $R_2$, $R_3$, and $R_4$ are, independently, H or $C_1$-$C_3$ alkyl.

In one embodiment, $R_5$, $R_6$, $R_7$, $R_8$, $R_9$, $R_{10}$, $R_{11}$, and $R_{12}$, are, independently, H, $C_1$-$C_4$ alkyl, $C_2$-$C_4$ alkenyl, or $C_2$-$C_4$ alkynyl.

In one embodiment, $R_{13}$ and $R_{14}$ are, independently at each occurrence, H or $C_1$-$C_3$ alkyl.

In one embodiment, $L_g$ is Br.

In one embodiment, $L_g$—$(CR_{13}R_{14})_k$—D is 6-Bromomethyl-quinoxaline.

In one embodiment, the method further comprises brominating 6-methylquinoxaline, thereby forming $L_g$—$(CR_{13}R_{14})_k$—D. In one embodiment, bromination is achieved using N-bromosuccinimide ("NBS") (e.g., 1.1 equivalents) and azobisisobutyronitrile ("AIBN") (e.g., 2.4 mol %) of in carbon tetrachloride ("$CCl_4$") at reflux.

In one embodiment, the method further comprises reacting 4-methylphenylene-1,2-diamine with glyoxal, thereby forming said 6-methylquinoxaline.

In one embodiment, the base comprises potassium carbonate or N,N-diisopropylethylamine.

In one embodiment, the solvent comprises at least one of acetone, acetonitrile ("MeCN"), dimethylsulfoxide ("DMSO"), and tetrahydrofuran ("THF").

In one embodiment, the base comprises potassium carbonate and said solvent comprises acetone. In one embodiment, 2 equivalents of potassium carbonate are used.

In one embodiment, 1 equivalent of $L_g$—$(CR_{13}R_{14})_k$—D is used.

In one embodiment, the compound of formula I has formula:

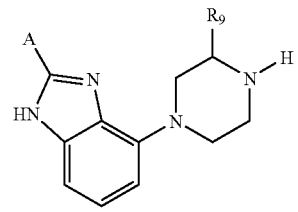

wherein:

A is optionally substituted aryl and $R_9$ is H or $C_1$-$C_4$ alkyl.

In one embodiment, A is phenyl substituted with $C_1$-$C_6$ alkyl, $C_2$-$C_6$ alkenyl, $C_2$-$C_6$ alkynyl, $NR_{22}R_{23}$, $CR_{24}(CF_3)_2$, $JR_{22}$, or $C(=O)R_{22}$, wherein J is O or $SO_m$, wherein m is 0, 1, or 2; $R_{22}$ and $R_{23}$ are, independently, H, $C_1$-$C_7$ alkyl, $C_2$-$C_7$ alkenyl, $C_2$-$C_7$ alkynyl, aryl, or heteroalkyl, each alkyl, alkenyl, alkynyl, aryl, or heteroalkyl being optionally substituted, alternatively, $R_{22}$ and $R_{23}$, taken together with the atoms to which they are attached, form an optionally substituted cyclic or optionally substituted heterocyclic group, e.g., of 3-8 ring members and the heteroatoms are selected from O, N and S, optionally substituted with $R_{20}$—E—$R_{21}$, wherein E is O, N, $NR_{21}$, or $SO_m$, $R_{20}$ and $R_{21}$ are, independently, H, $C_1$-$C_3$ alkyl, or heteroalkyl, alternatively, $R_{20}$ and $R_{21}$, taken together with the atoms to which they are attached, form a cyclic or heterocyclic group, e.g., of 3-8 ring members and the heteroatoms are selected from O, N and S; and $R_{24}$ is H, or OH.

In one embodiment, the method further comprises reacting a compound having formula

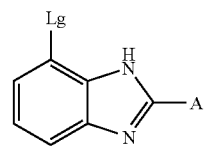

with a compound having formula

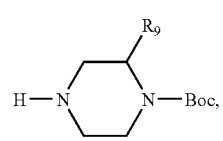

thereby forming said compound of Formula II. In one embodiment, $L_g$ is Br. In one embodiment, the reacting is carried out in toluene-THF in the presence of 5 mol % of $Pd_2(dba)_3$ and 10 mol % of CyMAP ligand with 3 equivalents of solid lithium hexamethyldisilazide ("LiHMDS").

In one embodiment, the method further comprises chlorinating a compound having formula

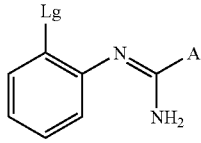

with N-chlorosuccinimide ("NCS") in methanol, and reacting the resulting N-chloride with potassium carbonate, thereby forming said compound having formula

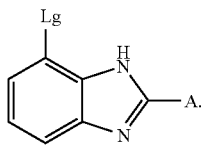

In one embodiment, the method further comprises reacting a compound having formula

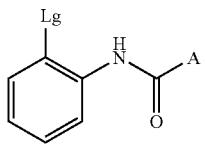

with thionyl chloride to form an imidoyl chloride, and reacting said imidoyl chloride with aqueous ammonia, thereby forming said compound having formula

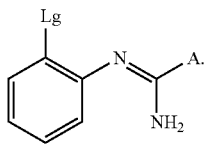

In one embodiment, the method further comprises reacting a compound of formula

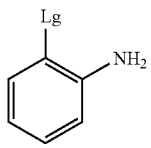

with a compound of formula

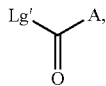

wherein $L_g'$ is a halogen, thereby forming said compound having formula

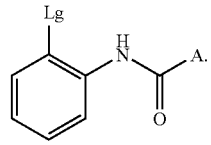

In one embodiment, $L_g'$ is Br. In one embodiment,

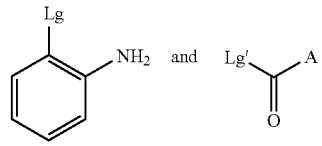

are combined under Schotten-Bauman conditions with NaHCO$_3$.

In one embodiment, A is optionally substituted aryl.

In one embodiment, A is aryl substituted with $C_1$-$C_6$ alkyl, $C_2$-$C_6$ alkenyl, $C_2$-$C_6$ alkynyl, $NR_{22}R_{23}$, $CR_{24}(CF_3)_2$, $JR_{22}$, or $C(=O)R_{22}$, wherein J is O or $SO_m$, wherein m is 0, 1, or 2; $R_{22}$ and $R_{23}$ are, independently, H, $C_1$-$C_7$ alkyl, $C_2$-$C_7$ alkenyl, $C_2$-$C_7$ alkynyl, aryl, or heteroalkyl, each alkyl, alkenyl, alkynyl, aryl, or heteroaryl being optionally substituted, alternatively, $R_{22}$ and $R_{23}$, taken together with the atoms to which they are attached, form an optionally substituted cyclic or optionally substituted heterocyclic group, e.g., of 3-8 ring members and the heteroatoms are selected from O, N and S optionally substituted with $R_{20}$—E—$R_{21}$, wherein E is O, N, $NR_{21}$, or $SO_m$, $R_{20}$ and $R_{21}$ are, independently, H, $C_1$-$C_3$ alkyl, or heteroalkyl, alternatively, $R_{20}$ and $R_{21}$, taken together with the atoms to which they are attached, form a cyclic or heterocyclic group, e.g., of 3-8 ring members and the heteroatoms are selected from O, N and S; and $R_{24}$ is H, or OH.

In one embodiment, A is para t-butyl phenyl.

In one embodiment, the method further comprises adding 2 equivalents of ethereal HCl to a solution of the compound having Formula II in ethanol, thereby forming a salt.

In one embodiment, the present invention comprises a method comprising reacting a compound having Formula III:

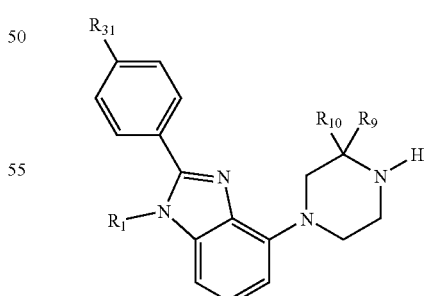

wherein:

$R_1$ is H or alkyl;

$R_9$ and $R_{10}$, are, independently, H, alkyl, alkenyl, or alkynyl, each alkyl, alkenyl, or alkynyl being optionally substituted; and $R_{31}$ is $C_1$-$C_6$ alkyl, $C_2$-$C_6$ alkenyl, $C_2$-$C_6$ alkynyl, $NR_{22}R_{23}$, $CR_{24}(CF_3)_2$, $JR_{22}$, or $C(=O)R_{22}$, wherein J is O or $SO_m$, wherein m is 0, 1, or 2;

$R_{22}$ and $R_{23}$ are, independently, H, $C_1$-$C_7$ alkyl, $C_2$-$C_7$ alkenyl, $C_2$-$C_7$ alkynyl, aryl, or heteroalkyl, each alkyl, alkenyl, alknyl, aryl, or heteroalkyl being optionally substituted, alternatively, $R_{22}$ and $R_{23}$, taken together with the atoms to which they are attached, form a cyclic or heterocyclic group, e.g., of 3-8 ring members and the heteroatoms are selected from O, N and S, optionally substituted with $R_{20}$—E—$R_{21}$, wherein E is O, N, $NR_{21}$, or $SO_m$, $R_{20}$ and $R_{21}$ are, independently, H, $C_1$-$C_3$ alkyl, or heteroalkyl, alternatively, $R_{20}$ and $R_{21}$, taken together with the atoms to which they are attached, form a cyclic or heterocyclic group, e.g., of 3-8 ring members and the heteroatoms are selected from O, N and S; and $R_{24}$ is H, or OH;

with a compound having formula:

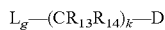

wherein:

D is heterocycloalkyl or heteroaryl, each optionally substituted;

$L_g$ is halogen or $OSO_2R_{32}$, wherein $R_{32}$ is alkyl, aryl, or fluoroalkyl, each optionally substituted;

k is 0, 1, 2, or 3; and $R_{13}$ and $R_{14}$ are, independently at each occurrence, H or optionally substituted alkyl, in an organic solvent in the presence of base, thereby forming a compound having Formula IV, or a pharmaceutically acceptable salt thereof:

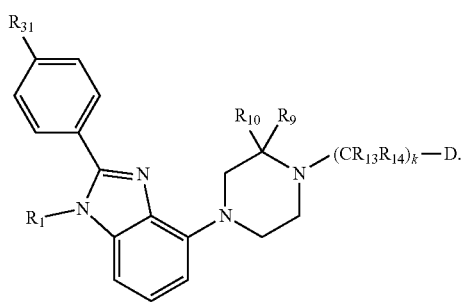

In one embodiment, D is optionally substituted heteroaryl.

In one embodiment, $R_1$ is H or $C_1$-$C_3$ alkyl.

In one embodiment, $R_9$ and $R_{10}$, are, independently, H, $C_1$-$C_4$ alkyl, $C_2$-$C_4$ alkenyl, or $C_2$-$C_4$ alkynyl.

In one embodiment, $R_{13}$ and $R_{14}$ are, independently at each occurrence, H or $C_1$-$C_3$ alkyl.

In one embodiment, $L_g$ is Br.

In one embodiment, $L_g$—$(CR_{13}R_{14})_k$—D is 6-Bromomethyl-quinoxaline.

In one embodiment, the method further comprises brominating 6-methylquinoxaline, thereby forming $L_g$—$(CR_{13}R_{14})_k$—D. In one embodiment, bromination is achieved using 1.1 equivalents of N-bromosuccinimide ("NBS") and 2.4 mol % of azobisisobutyronitrile ("AIBN") in carbon tetrachloride ("CCl$_4$") at reflux.

In one embodiment, the method further comprises reacting 4-methylphenylene-1,2-diamine with glyoxal, thereby forming said 6-methylquinoxaline.

In one embodiment, the base is potassium carbonate or N,N-diisopropylethylamine.

In one embodiment, the solvent includes at least one of acetone, acetonitrile ("MeCN"), dimethylsulfoxide ("DMSO"), and tetrahydrofuran ("THF").

In one embodiment, the base includes potassium carbonate and said solvent includes acetone.

In one embodiment, 2 equivalents of potassium carbonate are used.

In one embodiment, 1 equivalent of $L_g$—$(CR_{13}R_{14})_k$—D is used.

In one embodiment, the method further comprises reacting a compound having formula

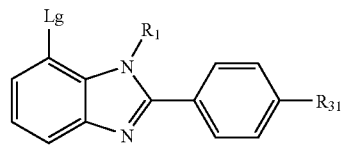

with a compound having formula

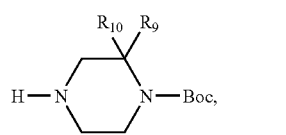

thereby forming said compound of Formula III. In one embodiment, $L_g$ is Br. In one embodiment, said reacting is carried out in toluene-THF in the presence of 5 mol % of $Pd_2(dba)_3$ and 10 mol % of CyMAP ligand with 3 equivalents of solid lithium hexamethyldisilazide ("LiHMDS").

In one embodiment, the method further comprises chlorinating a compound having formula

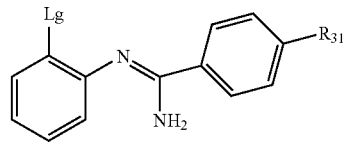

with N-chlorosuccinimide ("NCS") in methanol, and reacting the resulting N-chloride with potassium carbonate, thereby forming said compound having formula

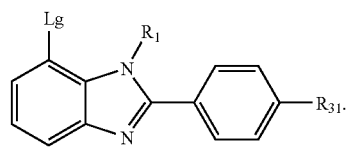

In one embodiment, the method further comprises reacting a compound having formula

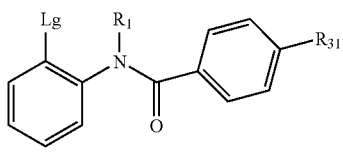

with thionyl chloride to form an imidoyl chloride, and reacting said imidoyl chloride with aqueous ammonia, thereby forming said compound having formula

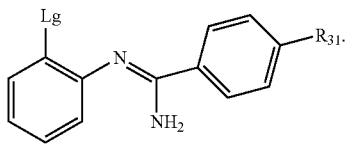

In one embodiment, the method further comprises reacting a compound of formula

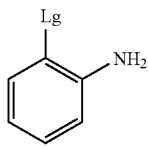

with a compound of formula

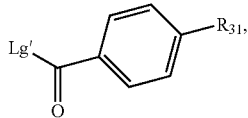

wherein $L_g'$ is a halogen, thereby forming said compound having formula

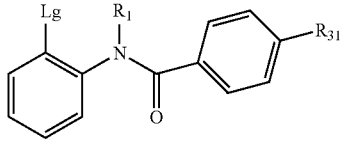

In one embodiment, $L_g'$ is Br. In one embodiment,

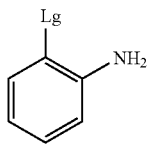

and

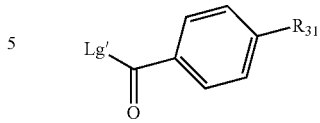

are combined under Schotten-Bauman conditions with $NaHCO_3$.

In one embodiment, $R_{31}$ is t-butyl.

In one embodiment, the method further comprises adding 2 equivalents of ethereal HCl to a solution of the compound having Formula IV in ethanol, thereby forming a salt.

In one embodiment, the present invention comprises a compound having Formula III:

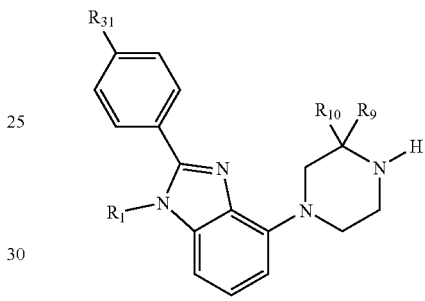

III wherein:

$R_1$ is H or alkyl;

$R_9$ and $R_{10}$, are, independently, H, alkyl, alkenyl, or alkynyl, each alkyl, alkenyl, or alkynyl being optionally substituted; and $R_{31}$ is $C_1$-$C_6$ alkyl, $C_2$-$C_6$ alkenyl, $C_2$-$C_6$ alkynyl, $NR_{22}R_{23}$, $CR_{24}(CF_3)_2$, $JR_{22}$, or $C(=O)R_{22}$, wherein J is O or $SO_m$, wherein m is 0, 1, or 2;

$R_{22}$ and $R_{23}$ are, independently, H, $C_1$-$C_7$ alkyl, $C_2$-$C_7$ alkenyl, $C_2$-$C_7$ alkynyl, aryl, or heteroalkyl, each alkyl, alkenyl, alkynyl, aryl, or heteroalkyl being optionally substituted, alternatively, $R_{22}$ and $R_{23}$, taken together with the atoms to which they are attached, form a cyclic or heterocyclic group, e.g., of 3-8 ring members and the heteroatoms are selected from O, N and S, optionally substituted with $R_{20}$—E—$R_{21}$, wherein E is O, N, $NR_{21}$, or $SO_m$, $R_{20}$ and $R_{21}$ are, independently, H, $C_1$-$C_3$ alkyl, or heteroalkyl, alternatively, $R_{20}$ and $R_{21}$, taken together with the atoms to which they are attached, form a cyclic or heterocyclic group, e.g., of 3-8 ring members and the heteroatoms are selected from O, N and S; and $R_{24}$ is H, or OH.

In one embodiment, $R_9$ is H or $CH_3$.

In one embodiment, $R_{31}$ is $C_1$-$C_6$ alkyl.

In one embodiment, $R_{31}$ is t-butyl.

DEFINITIONS

All recitations of a group, such as alkyl, are understood for the purposes of this specification to encompass both substituted and unsubstituted forms.

The term "alkyl", as used herein, whether used alone or as part of another group, refers to a substituted or unsubstituted aliphatic hydrocarbon chain and includes, but is not limited to, straight and branched chains containing from 1 to 12 carbon atoms, or in some instances, from 1 to 6 carbon atoms, unless explicitly specified otherwise. For example, methyl, ethyl, propyl, isopropyl, butyl, i-butyl and t-butyl are encompassed by the term "alkyl." $C_1$-$C_6$ alkyl includes straight and branched chain aliphatic groups having from 1 to 6 carbons. Specifically included within the definition of "alkyl" are those aliphatic hydrocarbon chains that are optionally substituted. In one embodiment, an alkyl is substituted with one or more of the following groups: —V-halogen, —V—$N_3$, —V—$NO_2$, —V—CN, —V—OR', —V—SR', —V—$SO_2$R', —V—$SO_2$N(R')$_2$, —V—N(R')$_2$, —V—COR', —V—$CO_2$R', —V—NR'$CO_2$R', —V—NR'COR', —V—NR'CONR', —V—CON(R')$_2$, —C(OH)(CF$_3$)$_2$, —CH(CF$_3$)$_2$, or —C(CF$_3$)$_3$, wherein each R' is independently hydrogen or unsubstituted ($C_1$-$C_6$)-alkyl; and wherein each V is independently a bond or ($C_1$-$C_6$)-alkyl.

Likewise, the term "heteroalkyl" as used herein refers to an alkyl group (e.g., of 2-7 carbon atoms) in which 1-3 carbon atoms within the carbon backbone are independently replaced by O, S or N heteroatoms. For example, methoxy, ethoxy, methylthio, ethylthio, methylamine, ethylamine, dimethylamine, diethylamine, methoxy methyl, ethoxymethyl, aminomethyl, and hydroxymethyl are encompassed by the term "heteroalkyl." In one embodiment, a heteroalkyl is substituted with one or more of the following groups: —V-halogen, —V—$N_3$, —V—$NO_2$, —V—CN, —V—OR', —V—SR', —V—$SO_2$R', —V—$SO_2$N(R')$_2$, —V—N(R')$_2$, —V—COR', —V—$CO_2$R', —V—NR'$CO_2$R', —V—NR'COR', —V—NR'CONR', —V—CON(R')$_2$, —C(OH)(CF$_3$)$_2$, —CH(CF$_3$)$_2$, or —C(CF$_3$)$_3$, wherein each R' is independently hydrogen or unsubstituted ($C_1$-$C_6$)-alkyl; and wherein each V is independently a bond or ($C_1$-$C_6$)-alkyl.

The carbon number as used in the definitions herein refers to carbon backbone and carbon branching, but does not include carbon atoms of the substituents, such as alkoxy substitutions and the like.

The term "alkenyl", as used herein, whether used alone or as part of another group, refers to a substituted or unsubstituted hydrocarbon chain and includes, but is not limited to, straight and branched chains having 2 to 8 carbon atoms and containing at least one double bond. In one embodiment, the alkenyl moiety has 1 or 2 double bonds. Such alkenyl moieties may exist in the E or Z conformations and the compounds of this invention include both conformations. $C_2$-$C_6$ alkenyl includes a 2 to 6 carbon straight or branched chain having at least one carbon-carbon double bond. Specifically included within the definition of "alkenyl" are those aliphatic hydrocarbon chains that are optionally substituted. In one embodiment, a heteroatom, such as O, S or N, attached to an alkenyl is not attached to a carbon atom that is bonded to a double bond. In one embodiment, an alkenyl is substituted with one or more of the following groups: —V-halogen, —V—$N_3$, —V—$NO_2$, —V—CN, —V—OR', —V—SR', —V—$SO_2$R', —V—$SO_2$N(R')$_2$, —V—N(R')$_2$, —V—COR', —V—$CO_2$R', —V—NR'$CO_2$R', —V—NR'COR', —V—NR'CONR', —V—CON(R')$_2$, —C(OH)(CF$_3$)$_2$, —CH(CF$_3$)$_2$, or —C(CF$_3$)$_3$, wherein each R' is independently hydrogen or unsubstituted ($C_1$-$C_6$)-alkyl; and wherein each V is independently a bond or ($C_1$-$C_6$)-alkyl.

The term "alkynyl" refers to a hydrocarbon moiety containing at least one carbon-carbon triple bond. $C_2$-$C_6$ alkynyl includes a 2 to 6 carbon straight or branched chain having at least one carbon-carbon triple bond. In one embodiment, an alkynyl is substituted with one or more of the following groups: —V-halogen, —V—$N_3$, —V—$NO_2$, —V—CN, —V—OR', —V—SR', —V—$SO_2$R', —V—$SO_2$N(R')$_2$, —V—N(R')$_2$, —V—COR', —V—$CO_2$R', —V—NR'$CO_2$R', —V—NR'COR', —V—NR'CONR', —V—CON(R')$_2$, —C(OH)(CF$_3$)$_2$, —CH(CF$_3$)$_2$, or —C(CF$_3$)$_3$, wherein each R' is independently hydrogen or unsubstituted ($C_1$-$C_6$)-alkyl; and wherein each V is independently a bond or ($C_1$-$C_6$)-alkyl.

The term "cycloalkyl" refers to a monocyclic, bicyclic, tricyclic, fused, bridged, or spiro monovalent saturated hydrocarbon moiety, wherein the carbon atoms are located inside or outside of the ring system, e.g., of 3-15 carbon atoms. Any suitable ring position of the cycloalkyl moiety may be covalently linked to the defined chemical structure. Examples of cycloalkyl moieties include, but are not limited to, chemical groups such as cyclopropyl, cyclopropylmethyl, cyclobutyl, cyclopentyl, cyclohexyl, cyclohexylmethyl, cyclohexylethyl, cycloheptyl, norbornyl, adamantyl, spiro[4.5]decanyl, and homologs, isomers, and the like. $C_3$-$C_6$ cycloalkyl includes monocyclic, saturated rings of 3 to 6 carbons. In one embodiment, a cycloalkyl is substituted with one or more of the following groups: —V—H, —V-halogen, —V—$N_3$, —V—$NO_2$, —V—CN, —V—OR', —V—SR', —V—$SO_2$R', —V—$SO_2$N(R')$_2$, —V—N(R')$_2$, —V—COR', —V—$CO_2$R', —V—NR'$CO_2$R', —V—NR'COR', —V—NR'CONR', —V—CON(R')$_2$, —C(OH)(CF$_3$)$_2$, —CH(CF$_3$)$_2$, or —C(CF$_3$)$_3$, wherein each R' is independently hydrogen or unsubstituted ($C_1$-$C_6$)-alkyl; and wherein each V is independently a bond or ($C_1$-$C_6$)-alkyl.

"Heteroaryl" refers to a 5 to 6 membered aromatic heterocyclic ring which contains from 1 to 4 heteroatoms selected from the group consisting of oxygen, nitrogen, and sulfur atoms in the ring and may be fused with a carbocyclic or heterocyclic ring at any possible position (e.g. of 5-8 ring atoms, the fused heterocyclic ring containing from 1 to 4 heteroatoms selected from the group consisting of oxygen, nitrogen, and sulfur atoms in the ring). In one embodiment, a heteroaryl is substituted with one or more of the following groups: —V—H, —V-halogen, —V—$N_3$, —V—$NO_2$, —V—CN, —V—OR', —V—SR', —V—$SO_2$R', —V—$SO_2$N(R')$_2$, —V—N(R')$_2$, —V—COR', —V—$CO_2$R', —V—NR'$CO_2$R', —V—NR'COR', —V—NR'CONR', —V—CON(R')$_2$, —C(OH)(CF$_3$)$_2$, —CH(CF$_3$)$_2$, or —C(CF$_3$)$_3$, wherein each R' is independently hydrogen or unsubstituted ($C_1$-$C_6$)-alkyl; and wherein each V is independently a bond or ($C_1$-$C_6$)-alkyl.

"Heterocycloalkyl" refers to a 5 to 7-membered saturated ring containing carbon atoms and from 1 to 2 heteroatoms selected from N, O, and S. In one embodiment, a heterocycloalkyl is substituted with one or more of the following: =O, —V—H, —V-halogen, —V—$N_3$, —V—$NO_2$, —V—CN, —V—OR', —V—SR', —V—$SO_2$R', —V—$SO_2$N(R')$_2$, —V—N(R')$_2$, —V—COR', —V—$CO_2$R', —V—NR'$CO_2$R', —V—NR'COR', —V—NR'CONR', —V—CON(R')$_2$, —C(OH)(CF$_3$)$_2$, —CH(CF$_3$)$_2$, or —C(CF$_3$)$_3$, wherein each R' is independently hydrogen or unsubstituted ($C_1$-$C_6$)-alkyl; and wherein each V is independently a bond or ($C_1$-$C_6$)-alkyl.

The term "aryl" as used herein as a group or part of a group refers to an aromatic carbocyclic ring, e.g., of from 6 to 14 carbon atoms such as phenyl, which may be optionally substituted. "Phenyl", as used herein, whether used alone or as part of another group, refers to a substituted or unsubstituted phenyl group. In one embodiment, an aryl group such as phenyl is substituted with one or more of the following: —V—H, —V-halogen, —V—$N_3$, —V—$NO_2$, —V—CN, —V—OR', —V—SR', —V—$SO_2$R', —V—$SO_2$N(R')$_2$, —V—N(R')$_2$, —V—COR', —V—$CO_2$R', —V—NR'CO$_2$R', —V—NR'COR', —V—NR'CONR', —V—CON(R')$_2$, —C(OH)(CF$_3$)$_2$, —CH(CF$_3$)$_2$, or —C(CF$_3$)$_3$, wherein each R' is independently hydrogen or unsubstituted (C$_1$-C$_6$)-alkyl; and wherein each V is independently a bond or (C$_1$-C$_6$)-alkyl. Additional substituents on aryl are illustrated above in connection with A when phenyl in paragraph.

An optionally substituted moiety may be substituted with one or more substituents, examples of which are as illustrated herein. In one embodiment, an "optionally substituted" moiety is substituted with one or more of the following groups: =O, —VH, —V-halogen, —V—N$_3$, —V—NO$_2$, —V—CN, —V—OR', —V—SR', —V—SO$_2$R', —V—SO$_2$N(R')$_2$, —V—N(R')$_2$, —V—COR', —V—CO$_2$R', —V—NR'CO$_2$R', —V—NR'COR', —V—NR'CONR', —V—CON(R')$_2$, —C(OH)(CF$_3$)$_2$, —CH(CF$_3$)$_2$, or —C(CF$_3$)$_3$, wherein each R' is independently hydrogen or unsubstituted (C$_1$-C$_6$)-alkyl or phenyl; and wherein each V is independently a bond or (C$_1$-C$_6$)-alkyl.

When such moieties are substituted, for example, they may typically be mono-, di-, tri- or persubstituted. Examples for a halogen substituent include 1-bromo vinyl, 1-fluoro vinyl, 1,2-difluoro vinyl, 2,2-difluorovinyl, 1,2,2-trifluorovinyl, 1,2-dibromo ethane, 1,2 difluoro ethane, 1-fluoro-2-bromo ethane, CF$_2$CF$_3$, CF$_2$CF$_2$CF$_3$, and the like.

The term halogen includes bromine, chlorine, fluorine, and iodine.

For the sake of simplicity, connection points ("-") are not depicted. When an atom or compound is described to define a variable, it is understood that it is intended to replace the variable in a manner to satisfy the valency of the atom or compound. For example, if "X*" was C(R*)=C(R*), both carbon atoms form a part of the ring in order to satisfy their respective valences. Likewise, when divalent substituents are presented, it is understood that they are not limited to the order listed, for example, as used in this specification "OCH$_2$" encompasses CH$_2$O and OCH$_2$.

As used herein, a compound of the present invention also includes a pharmaceutically acceptable salt of a compound of the present invention. The term "pharmaceutically acceptable salt" as used herein refers to a salt of an acid and a basic nitrogen atom of a compound of the present invention. Exemplary salts include, but are not limited to, sulfate, citrate, acetate, oxalate, chloride, hydrochloride, bromide, hydrobromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, napthalenesulfonate, propionate, succinate, fumarate, maleate, malonate, mandelate, malate, phthalate, and pamoate. The term "pharmaceutically acceptable salt" as used herein also refers to a salt of a compound of the present invention having an acidic functional group, such as a carboxylic acid functional group, and a base. Exemplary bases include, but are not limited to, hydroxide of alkali metals including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—(C$_1$-C$_6$)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like. The term "pharmaceutically acceptable salt" also includes a hydrate of a compound of the present invention.

The term "patient", as used herein, refers to a mammal, in one embodiment, a human.

The terms "administer", "administering", or "administration", as used herein, refer to either directly administering a compound or composition to a patient, or administering a prodrug derivative or analog of the compound to the patient, which will form an equivalent amount of the active compound or substance within the patient's body.

The term "carrier", as used herein, shall encompass carriers, excipients, and diluents.

The term "tautomer" as used herein refers to compounds produced by the phenomenon wherein a proton of one atom of a molecule shifts to another atom. See, Jerry March, *Advanced Organic Chemistry: Reactions, Mechanisms and Structures*, Fourth Edition, John Wiley & Sons, pages 69-74 (1992).

The compounds of this invention may contain an asymmetric carbon atom and some of the compounds of this invention may contain one or more asymmetric centers and may thus give rise to optical isomers and diastereomers. While shown without respect to stereochemistry in formula I, the present invention includes such optical isomers and diastereomers; as well as the racemic and resolved, enantiomerically pure R and S stereoisomers; as well as other mixtures of the R and S stereoisomers and pharmaceutically acceptable salts thereof. Where a stereoisomer is provided, it may in some embodiments be provided substantially free of the corresponding enantiomer. Thus, an enantiomer substantially free of the corresponding enantiomer refers to a compound that is isolated or separated via separation techniques or prepared free of the corresponding enantiomer. "Substantially free", as used herein, means that the compound is made up of a significantly greater proportion of one stereoisomer, in one embodiment, less than about 50% of the other, in another embodiment, less than about 75%, and in yet another embodiment, less than about 90%, in one embodiment, less than about 95%, in another embodiment, less than about 98%, and in yet another embodiment, less than about 99%.

The terms "effective amount", "therapeutically effective amount" and "effective dosage" as used herein, refer to the amount of a compound, that, when administered to a patient, is effective to at least partially ameliorate (and, in other embodiments, cure) a condition form which the patient is suspected to suffer.

Compounds of the present invention have been found to act as GnRH receptor antagonists. They are therefore useful in the treatment of prostate cancer, endometriosis, uterine fibroids, uterine cancer, breast cancer, ovarian cancer, testicular cancer, primary hirsutism, or LH surge. In addition, they are useful as oral contraceptives. The present invention thus provides pharmaceutical compositions comprising at least one compound of the present invention and one or more pharmaceutically acceptable carriers, excipients, or diluents.

Examples of such carriers are well known to those skilled in the art and are prepared in accordance with acceptable pharmaceutical procedures, such as, for example, those described in *Remington's Pharmaceutical Sciences,* 17th edition, ed. Alfonoso R. Gennaro, Mack Publishing Company, Easton, Pa. (1985), which is incorporated herein by reference in its entirety. Pharmaceutically acceptable carriers are those that are compatible with the other ingredients in the formulation and biologically acceptable.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or encapsulating materials. They are formulated in conventional manner, for example, in a manner similar to that used for known antihypertensive agents, diuretics and β-blocking agents. Oral formulations containing the active compounds of this invention may comprise any conventionally used oral forms, including tablets, capsules, buccal forms, troches, lozenges and oral liquids, suspensions or solutions. In powders, the carrier is a finely divided solid, which is an admixture with the finely divided active ingredient. In tablets, the active ingredient is mixed with a carrier having the necessary compression properties in suitable proportions and compacted in the shape and size desired. The powders and tablets in one embodiment contain up to 99% of the active ingredient.

Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc.

Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes and ion exchange resins. Exemplary surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colliodol silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or fruit juice, containing appropriate solubilizers or emulsifiers as needed.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, including sodium carboxymethyl cellulose solution), alcohols (including monohydric alcohols and polyhydric alcohols, e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration may be in either liquid or solid form.

In one embodiment, the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. Such unit dosage form may contain from about 1 mg/kg to about 250 mg/kg, and may given in a single dose or in two or more divided doses. Such doses may be administered in any manner useful in directing the active compounds herein to the recipient's bloodstream, including orally, via implants, parenterally (including intravenous, intraperitoneal and subcutaneous injections), rectally, vaginally, and transdermally. Such administrations may be carried out using the present compounds, or pharmaceutically acceptable salts thereof, in lotions, creams, foams, patches, suspensions, solutions, and suppositories (rectal and vaginal).

When administered for the treatment or inhibition of a particular disease state or disorder, it is understood that the effective dosage may vary depending upon the particular compound utilized, the mode of administration, the condition, and severity thereof, of the condition being treated, as well as the various physical factors related to the individual being treated. In therapeutic application, compounds of the present invention are provided to a patient already suffering from a disease in an amount sufficient to cure or at least partially ameliorate the symptoms of the disease and its complications. An amount adequate to accomplish this is defined as a "therapeutically effective amount". The dosage to be used in the treatment of a specific case must be subjectively determined by the attending physician. The variables involved include the specific condition and the size, age and response pattern of the patient.

In some cases it may be desirable to administer the compounds directly to the airways in the form of an aerosol. For administration by intranasal or intrabrochial inhalation, the compounds of this invention may be formulated into an aqueous or partially aqueous solution.

The compounds of this invention may be administered parenterally or intraperitoneally. Solutions or suspensions of these active compounds as a free base or pharmaceutically acceptable salt may be prepared in water suitably mixed with a surfactant such as hydroxyl-propylcellulose. Dispersions may also be prepared in glycerol, liquid polyethylene glycols and mixtures thereof in oils. Under ordinary conditions of storage and use, these preparations contain a preservative to inhibit the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The compounds of this invention can be administered transdermally through the use of a transdermal patch. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream, such as a semi-permeable membrane covering a reservoir containing the active ingredient with or without a carrier, or a matrix containing the active ingredient. Other occlusive devices are known in the literature.

The compounds of this invention may be administered rectally or vaginally in the form of a conventional suppository. Suppository formulations may be made from traditional materials, including cocoa butter, with or without the addition of waxes to alter the suppository's melting point, and glycerin. Water soluble suppository bases, such as polyethylene glycols of various molecular weights, may also be used.

In certain embodiments, the present invention is directed to prodrugs of compounds of the present invention. Various forms of prodrugs are known in the art, for example, as discussed in, for example, Bundgaard, (ed.), *Design of Prodrugs, Elsevier* (1985); Widder, et al. (ed.), *Methods in Enzymology*, vol. 4, Academic Press (1985); Krogsgaard-Larsen, et al. (ed.), *"Design and Application of Prodrugs"*, *Textbook of Drug Design and Development*, Chapter 5, 113-191 (1991), Bundgaard, et al., *Journal of Drug Delivery* reviews, 8:1-38 (1992), Bundgaard, J. of Pharmaceutical Sciences, 77:285 et seq. (1988); and Higuchi and Stella (eds.) *Prodrugs as Novel Drug Delivery Systems*, American Chemical Society (1975), each of which is incorporated by reference in its entirety.

It is understood that the dosage, regimen and mode of administration of these compounds can vary according to the malady and the individual being treated and, in some embodiments, is subject to the judgment of the medical practitioner involved. In one embodiment, the administration of one or more of the compounds herein begins at a low dose and is increased until the desired effects are achieved.

The compounds of the invention can be prepared using a variety of methods starting from commercially available compounds, known compounds, or compounds prepared by known methods. General synthetic routes to many of the compounds of the invention are included in the following schemes. It is understood by those skilled in the art that protection and deprotection steps not shown in the Schemes may be required for these syntheses, and that the order of steps may be changed to accommodate functionality in the target molecules.

Method of Making

Scheme 1 provides an overview of a method of making compounds of the Formula II. The individual steps labeled in Scheme 1 are described below.

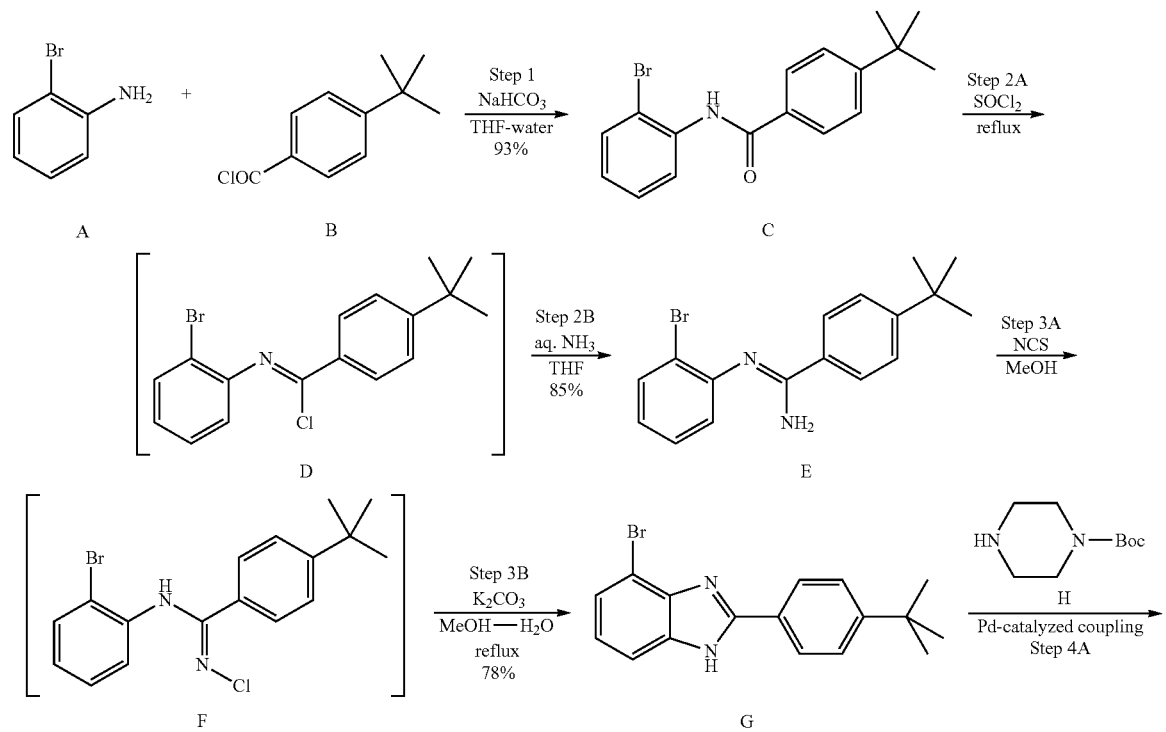

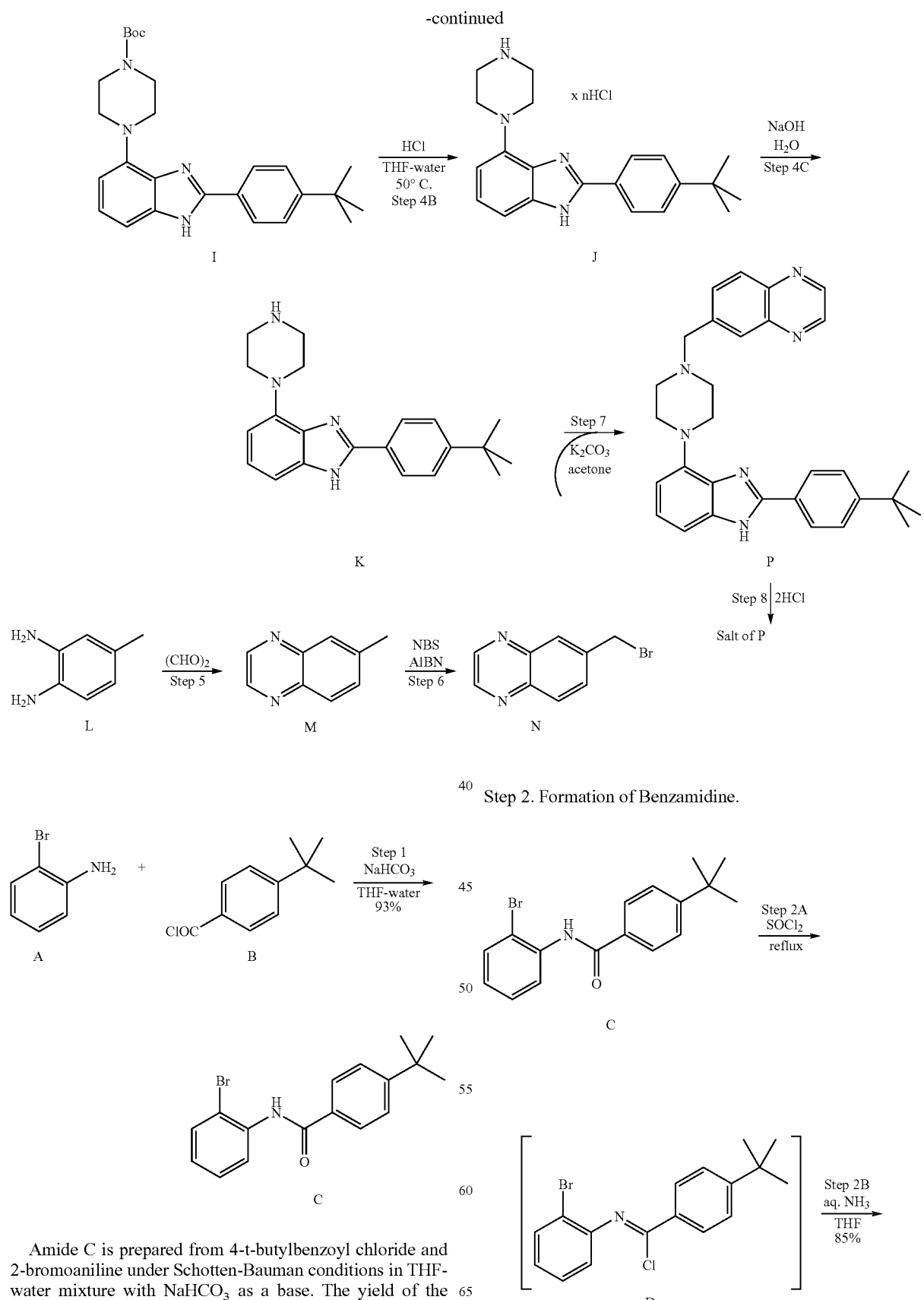
Step 2. Formation of Benzamidine.
Amide C is prepared from 4-t-butylbenzoyl chloride and 2-bromoaniline under Schotten-Bauman conditions in THF-water mixture with NaHCO₃ as a base. The yield of the isolated and recrystallized amide is above 90%, and no optimization is required.

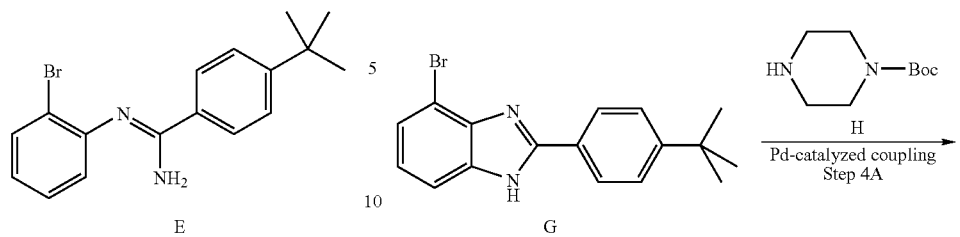

Benzamidine E is prepared by adaptation of the literature procedures (Artmonova, T. V.; Zhivich, A. V.; Dubinskii, M. Yu.; Koldobskii, G. I. *Synthesis* 1996, 12, 1428. Katritzky, A. R.; Tarraga, T. A. *Heterocycles* 1982, 18, 21). Amide C is converted to imidoyl chloride D by treatment with thionyl chloride at reflux. Reaction of D with aqueous ammonia gives the desired amidine E with the total yield of 70-85%.

Step 3. Preparation of 4-bromobenzimidazole

Amidine E is chlorinated with NCS in methanol at room temperature. Resulting N-chloride F is treated with potassium carbonate which causes the ring closure to benzimidazole G. The reaction gives consistent yields on any scale from less than a gram to almost 300 g. On the largest scale, however, an unexpected exotherm was observed when, after addition of potassium carbonate, the reaction mixture was being heated to effect the ring closure. The exotherm went unnoticed in smaller scale runs. Another safety point came to our attention after the large scale run. According to the *Bretherick's*, the combination of NCS and methanol may not be entirely safe. If safety is a concern, acetonitrile may be used instead of methanol with no deleterious effects on yield and purity.

Step 4. Pd-catalyzed Piperazine Coupling and Boc Removal

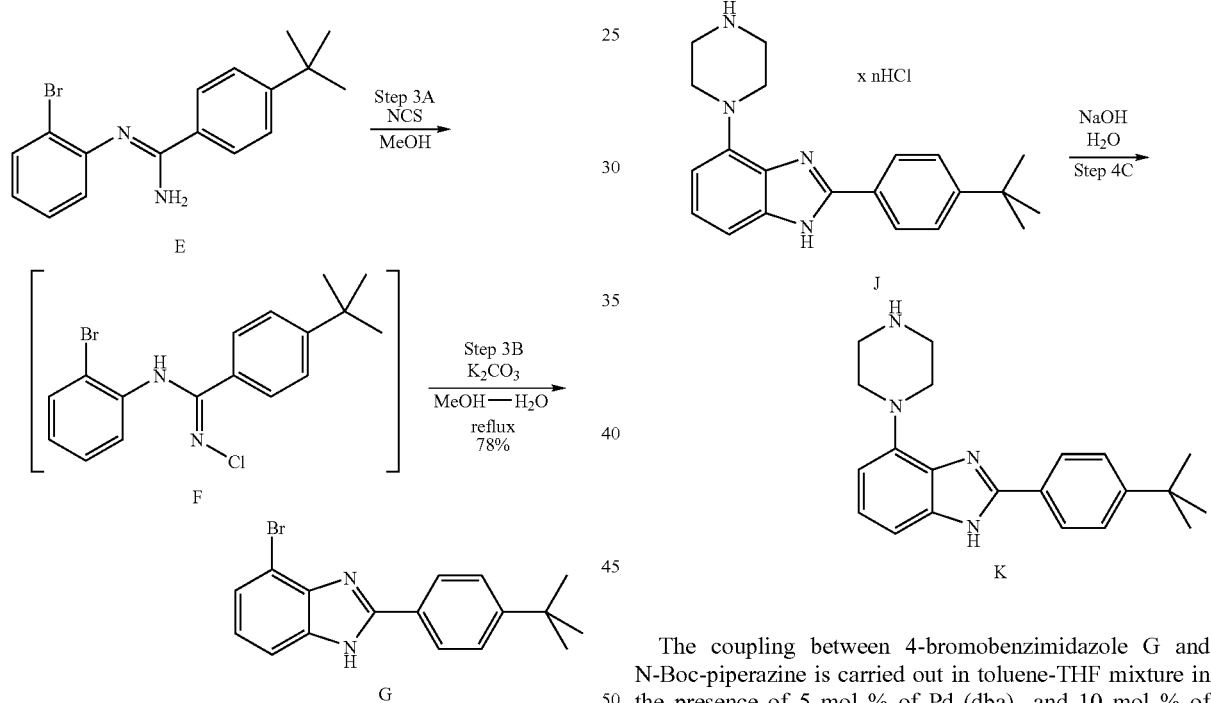

The coupling between 4-bromobenzimidazole G and N-Boc-piperazine is carried out in toluene-THF mixture in the presence of 5 mol % of $Pd_2(dba)_3$ and 10 mol % of CyMAP with 3 eq. of solid LiHMDS as the base. LiHMDS is dispensed in a plastic bag under nitrogen blanket, while the rest of the reagents are loaded in open air. The reaction is complete in about 1 hr at 50° C. and gives a mixture of products consisting of 80% of N-Boc-piperazinobenzimidazole I.

The mixture is enriched in I when it is isolated as a solid after aqueous workup (90% purity). This mixture is taken directly into the Boc-removal step. The deprotection is carried out with HCl in THF-water mixed solvent. The reagent and solvent ratios allow the deprotected product to crystallize out of the reaction mixture as an HCl salt J which is separated by filtration. The crystals came out further enriched in the desired product J (97% purity). The HCl salt J is purified by treatment of its warm aqueous solution with activated carbon. From the filtered solution, the free base is precipitated with 1

M NaOH solution and extracted with EtOAc. Final solid K is isolated in 42% yield (based on the amount of bromobenzimidazole) and is 98% pure.

Step 5. Preparation of 6-methylquinoxaline

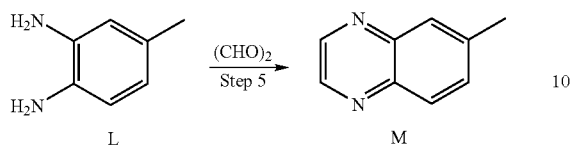

6-Methylquinoxaline M is prepared from 4-methylphenylene-1,2-diamine L and glyoxal. According to the literature precedents, glyoxal in this reaction could be used as either 40% aq. solution or a crystalline bisulfite adduct, both are commercially available. It was our finding that the bisulfite adduct gave a much cleaner reaction and higher yield of the product. The reaction is carried out in water at 60° C., the product M is isolated by extraction with ether and purified by distillation.

Step 6. Bromination of 6-methylquinoxaline

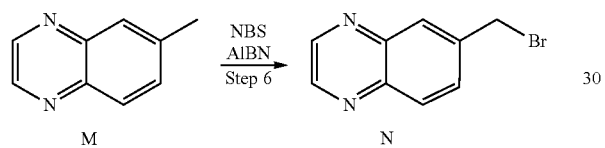

Several different combinations of the solvent (DCE, PhCl, PhH, CCl$_4$), radical initiator (Bz$_2$O$_2$, AIBN), temperature (45-85° C.) and time (1-24 hr) have been screened to determine the optimal set of conditions for radical bromination. The best result in terms of the mono- to bis-bromide ratios and isolated yield and purity of the mono-brominated product is observed with 1.1 eq. of NBS, 2.4 mol % of AIBN in CCl$_4$ at reflux for 1.5 hr. The pure mono-bromide crystallizes out of the reaction mixture and is separated by filtration. 6-Bromomethylquinoxaline decomposes fairly rapidly when stored in a vial at room temperature and has to be prepared at least within several days before use in the subsequent step.

Step 7. Alkylation of 4-piperazinobenzimidazole

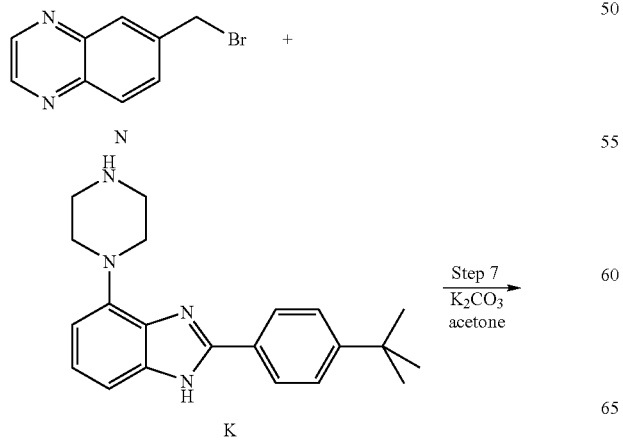

-continued

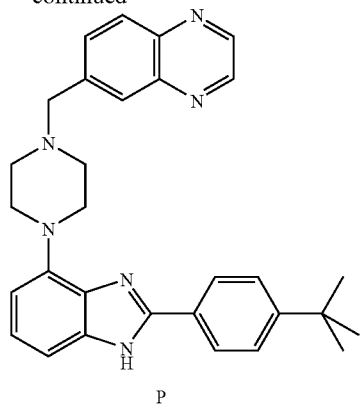

Alkylation is carried out with 1.0 eq of the bromide N and 2 eq of K$_2$CO$_3$ as a base in acetone at room temp. over 22 hr. The product is isolated by filtration, purified by multiple washes with water and dried in a vacuum desiccator over CaSO$_4$.

Step 8. Formation of the Salt Form

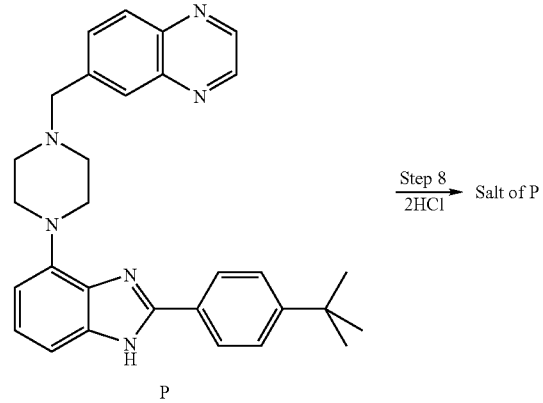

Dihydrochloride salt prepared was found to be the best of a series of possible formulations as judged by its crystallinity, solubility, stability, etc. The salt is prepared by adding 2 eq of ethereal HCl to a solution of the free base in ethanol. The salt is isolated by filtration.

One of skill in the art will recognize that the above Scheme and Steps can be adapted to produce the other compounds and pharmaceutically acceptable salts of compounds according to the present invention.

EXAMPLES

Example 1

LCMS analysis was done on an open access Agilent chromatograph with UV and mass detectors, 5 cm C18 column, 5 min gradient of 95% water to 95% MeCN. HPLC analysis was done on a Waters liquid chromatograph, 15 cm C18 column, 20 min runs with a 10 min gradient from 95% water to 95% MeCN (0.05% TFA) and 1 mL/min flow.

27

N-(2-bromophenyl)-4-tert-butylbenzamide

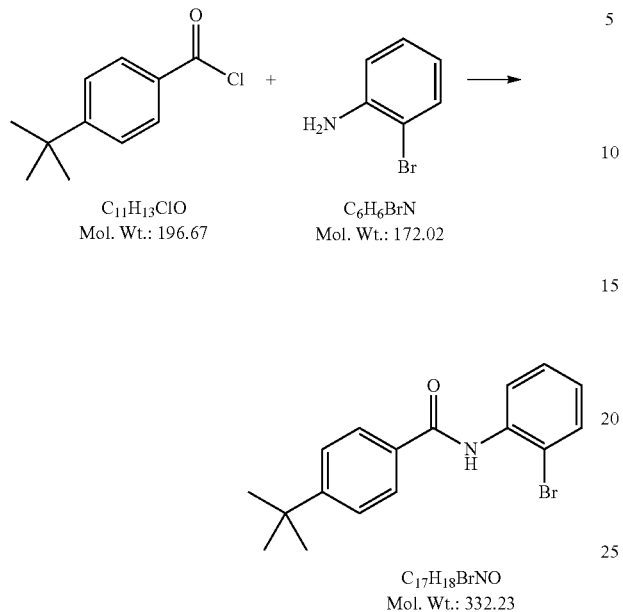

2-Bromoaniline (98%, Oakwood 005347, 214 g, 1.25 mol), NaHCO$_3$ (270 g, 3.2 mol), THF (500 mL) and water (500 mL) were placed into a 5-L round-bottom flask equipped with an overhead stirrer, thermometer and a 500-mL addition funnel. Solution of t-butyl benzoyl chloride (>98%, Fluka 19660, 250 mL, 1.37 mol) in 250 mL of THF was placed into the addition funnel and was added slowly (in 25 min) to the stirred mixture of reagents in the flask. (No external heating or cooling was administered, slight exotherm was observed raising the temperature inside the flask to 35° C.).

After the addition was complete, the reaction mixture was left stirring overnight (14 hr). LCMS analysis after that showed complete conversion to the amide (product peak @ 4.30 min, MH$^+$ 332$^{Br}$; by-product peak @ 4.74 min 2M+Na$^+$ 699 corresponds to tert-butylbenzoyl anhydride).

The liquid from the reaction flask was decanted off the precipitate into a sep. funnel, the aq. layer was separated and extracted with ether (2×150 mL). Inorganic salts left in the reaction flasks were washed with ether (2×100 mL). Combined organic solutions were further diluted with 200 mL of ether, washed with 50 mL of water, 100 mL of aq. 1 M HCl, 50 mL of aq. K$_2$CO$_3$ and 50 mL of brine. The resulting solution was dried with MgSO$_4$ and filtered through a cotton plug. The solvents were removed in vacuum, the oily residue solidified slowly into a white cake.

The cake was dissolved in approximately 100 mL of hot heptane, allowed to cool to r.t. and seeded with a couple of crystals of the amide. The product crystallized from the solution as white needles. The mixture was kept in a freezer for 14 hr. The crystals were quickly filtered through a paper filter, washed with cold petroleum ether and dried in air. Yield 384 g (93%) as colorless needles.

28

N-(2-bromophenyl)-4-tert-butylbenzamidine

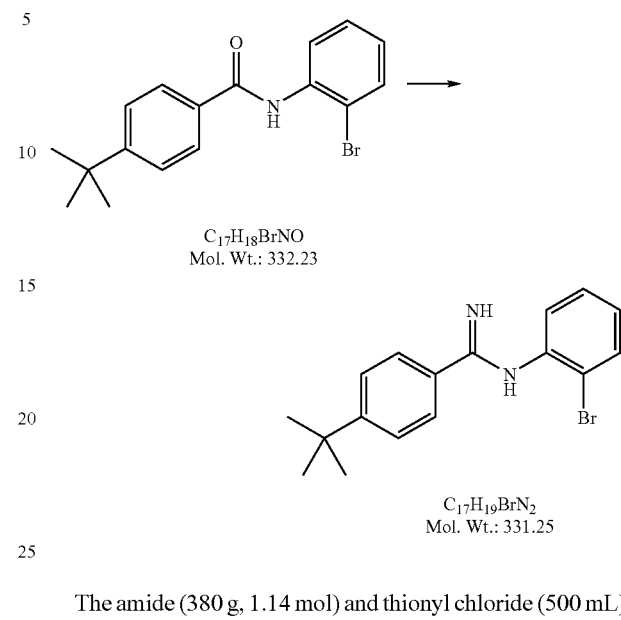

The amide (380 g, 1.14 mol) and thionyl chloride (500 mL) were placed into a 2-L round bottom flask equipped with a reflux condenser, attached to the HCl scrub line, and a mechanical stirrer. The clear yellow solution was heated at reflux for 14 hr. The excess of SOCl$_2$ was removed on rotary evaporator and the yellow oily residue (which solidified upon cooling to r.t. into a cake) was dissolved in 1.3 L of THF. To the resulting solution was added in one portion 0.7 L of concentrated aq. ammonia (no exotherm was observed) and the mixture was left stirring rapidly with an overhead stirrer for 14 hr. The aminolysis was monitored by LCMS: unreacted imidoyl chloride gave 2 peaks in UV trace with the mass data corresponding to the starting amide (MH$^+$ 332) and the [Ar—C≡NAr']$^+$ fragment (m/e 314).

Organic solvent was removed on a rotary evaporator. Light petroleum ether was added to the suspension of oil in water which caused crystallization of the product. The solid was filtered off, washed with petroleum ether and dried in a vacuum oven at 45° C. for 18 hr. Crude solid contained about 5% of the starting amide and 5% of unknown impurity. It was recrystallized from ethyl acetate-hexanes 1:1 mixture. Yield 320 g (85%) as colorless crystals.

4-bromo-2-(4-tert-butylphenyl)benzimidazole

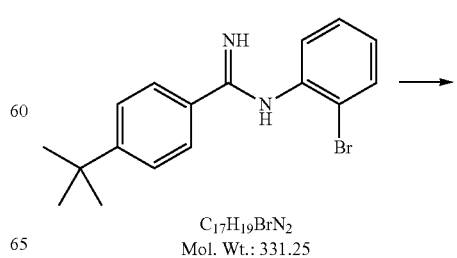

-continued

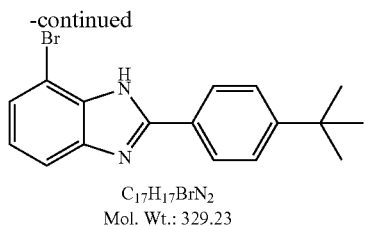

C$_{17}$H$_{17}$BrN$_2$
Mol. Wt.: 329.23

Solid NCS (11.5 g, 85 mmol) was added to a solution of the amidine in methanol (ca. 200 mL) and the mixture is kept at room temperature for 3-4 hours. Then solid K$_2$CO$_3$ (30 g, 210 mmol) and water (about 5 mL) were added and the mixture was heated at reflux for 1-15 min. The solvent was then removed in vacuum, the residue was partitioned between ether and water, the organic layer was separated and washed with water. Conc. aq. HCl (ca. 100 mmol) was added to the ether solution which caused formation of white crystalline precipitate of the benzimidazole salt. (Note. Water is necessary here for the solid to form. Addition of ethereal HCl to the dry solution of benzimidazole caused separation of an oil which crystallized only when water was added to it.) The solid was filtered (rather fine precipitate and bi-phasic mixture—took a long time to filter), washed with small amount of water and ether and dried in vacuum desiccator over P$_2$O$_5$. Yields 90% (R=Me), 91% (R=t-Bu).

To make a freebase of benzimidazole, the salt (23 g, 64 mmol) was stirred with aq. NaOH (70 mmol in 200 mL of water) and ether (300 mL) until everything dissolved. The ether layer was separated, washed with brine, dried with MgSO$_4$, filtered through a pad of Silica gel and evaporated to dryness. The solid residue was recrystallized from TBME—hexanes 1:1 mixture to afford 18.6 g (88%) of the product as a white solid.

2-(4-tert-butyl-phenyl)-4-piperazin-1-yl-1H-benzimidazole

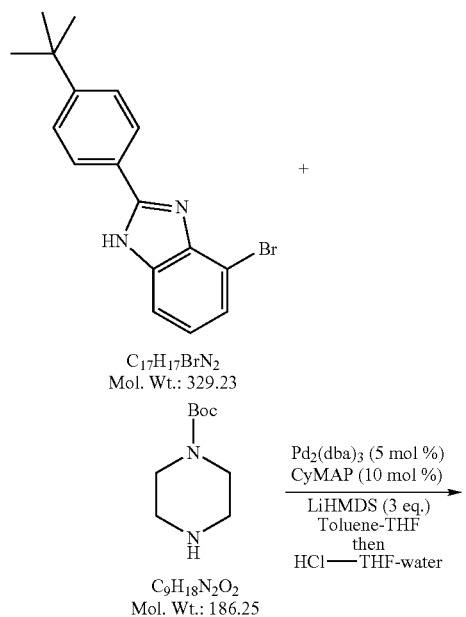

-continued

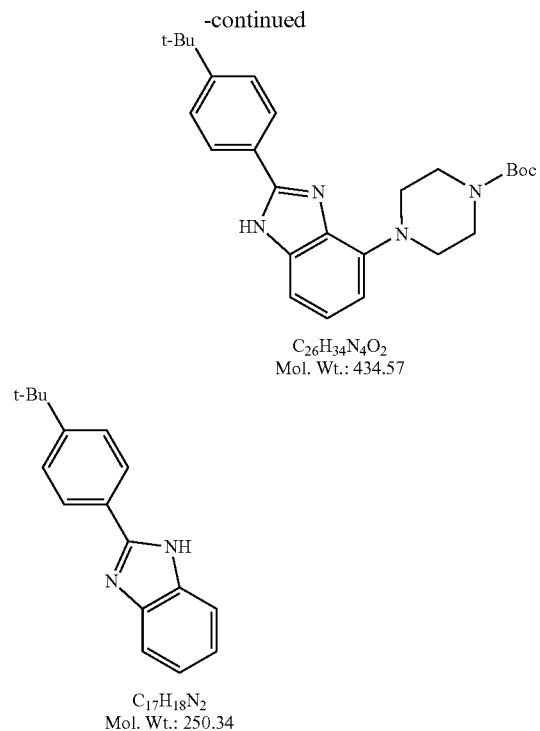

Pd-Catalyzed Coupling

A 3-L 3-neck round bottom flask equipped with an overhead stirrer, nitrogen inlet line, temperature probe, air condenser and placed in a heating mantle was charged with solid 4-bromobenzimidazole (103 g, 0.313 mol), solid N-Boc-piperazine (99%, Lancaster 13363, 64.0 g, 0.344 mol, 1.1 eq), solid 2-dicyclohexylphosphino-2'-(N,N-dimethylamino)biphenyl (CyMAP) (98%, Strem 15-1145, 12.3 g, 31.3 mmol, 10 mol %) and solid Pd$_2$(dba)$_3$ (Aldrich 32,877-4, 7.16 g, 15.6 mmol Pd, 5 mol %). The flask was purged with nitrogen. Toluene (1.0 L, ACS grade) and THF (250 mL, anhydrous grade) were added. The stirrer was turned on, the flask was purged with nitrogen. The temperature controller was set at 50° C., the heat was turned on.

Solid LiHMDS (160 g, 0.95 mol, 3 eq) was weighed under nitrogen and added in one portion to the reaction flask. The temperature of the reaction mixture went up from 25 to 46° C. in 4 min after the addition of the base. The solids in the reaction mixture dissolved completely resulting in a dark-brown solution. Nitrogen purge was stopped at this point, the reaction was left under nitrogen blanket, stirring rapidly, at 50° C.

The reaction mixture became heterogeneous after ca. 2 hr. The bottom phase was a dark-brown oil with viscosity of a syrup in the beginning but thickening after 4 hr. The lighter phase was a clear brownish solution. LCMS of both phases was taken to monitor the course of the reaction.

The heat was turned off after 5 hr at 50° C. The reaction mixture was allowed to cool to 45° C., then water (1 L) was added. The mixture was stirred rapidly until the bottom oily phase was broken up and partitioned between aqueous and organic layers. Some black solid remained insoluble in either phase and it was removed by filtering the mixture through a pad of Celite. The organic layer was then separated and washed once with 500 mL of water. The organic solvents were removed on a rotary evaporator (bath temp. 62° C., partial vacuum). To the residue of thick paste consistency was added 500 mL of toluene and evaporation was repeated to azeotropically remove water.

The resulting paste was triturated with 800 mL of TBME which resulted in a yellow suspension of a solid. The mixture was chilled in a bucket of ice, then the solid was filtered through a paper filter, washed with 500 mL of TBME and dried in air. Yield 95.4 g. Purity 90% (HPLC at 254 nm).

Boc Hydrolysis

The isolated solid from the coupling step (95 g) was placed into a 2-L Erlenmeyer equipped with a big magnetic stirrer. THF (475 mL) was added followed by 95 mL of 6 M HCl (prepared by dilution of commercial conc. HCl to double its volume). The resulting dark-red solution was heated to 50° C. with gentle stirring.

After 3 hours at 50° C., a crystalline precipitate separated from the solution. The heating was continued for 19 hr total. The source of heat was removed, THF (300 mL) was added to still warm mixture. The crystalline solid was filtered off on a paper filter and washed with 100 mL of 10:1 mixture of THF/water. The resulting gray solid was dried in air. Yield 71.3 g. Purity 97% (HPLC at 254 nm).

Preparation of the Free Base

The solid from the previous process was placed into a 4-L Erlenmeyer flask, water (1.6 L) and THF (200 mL) were added and the mixture was warmed up to 50° C. on a hot plate while gently stirring the mixture magnetically. The solid dissolved completely forming a dark-red cloudy solution. Activated carbon (12 g) was added and stirring at 50° C. was continued for 1 hr. Then about 20 g of Celite was added and the warm mixture was filtered through a Celite pad.

The pH of the filtrate was brought up to ca. 13 with 1 M aq. solution of NaOH. The product separated, forming a white milky suspension. EtOAc (1 L) was added and the mixture was stirred for 5 min to dissolve all the solid. Most of the aq. phase was removed and the remaining liquid had to be filtered through another pad of Celite to break up a very stable emulsion. The aqueous layer was extracted twice more with EtOAc (300 mL each), bringing the pH of the aq. solution to 13 before every extraction. The latter extracts were also filtered through a Celite pad. Combined organic layers were washed once with 200 mL of water, then evaporated on a rotary evaporator to dryness. The remaining water was removed by azeotropic distillation of 400 mL of toluene (at 65° C., slight vacuum). Yield 43.6 g (42% from bromobenzimidazole) as a light-yellow powder (amorphous). Purity 98% (HPLC at 254 μm), largest single impurity 0.3%.

6-Methylquinoxaline

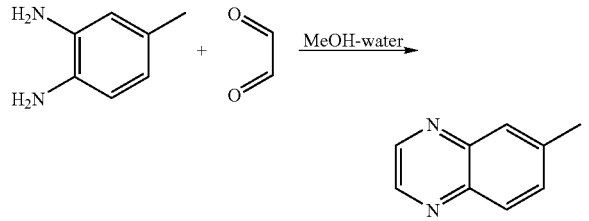

A solution of 3,4-diaminotoluene (Aldrich, 100 g, 0.82 mol) in 600 mL of hot water (temp. 70-75° C.) was added rapidly to a 60° C. slurry of glyoxal-sodium bisulfite adduct (Aldrich, 239.5 g, 0.9 mol, 1.1 eq) in 400 mL of water. The resulting dark-brown clear solution was heated at 60° C. for 1 hr, then 5 g (0.02 mol) of additional glyoxal adduct was added. The mixture was allowed to cool to r.t. and filtered through a paper filter. The filtrate was neutralized with 5 M aq. NaOH to pH 7.5-7.8 and then extracted with ether (4×400 mL). The extract was dried over $Na_2SO_4$ and concentrated on a rotary evaporator to afford 92 g of brown oil which was distilled in vacuum (bp. 100-102° C. at 10 mm Hg; Cavagnol, J. C.; Wiselogle, F. Y. J. Am. Chem. Soc. 1947, 69, 795; 86° C. at 1 mm Hg). Yield 89 g (75%) as a pale-yellow oil.

6-Bromomethylquinoxaline (1) (De Selms, R. C.; Greaves, R. J., Scheigh, W. R. J. Het. Chem. 1974, 11, 595)

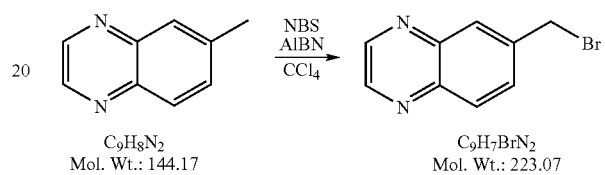

$C_9H_8N_2$
Mol. Wt.: 144.17

$C_9H_7BrN_2$
Mol. Wt.: 223.07

Bromomethylquinoxaline is unstable and decomposes when stored for long time. It should be used up within a day or two of its preparation.

To a clear solution of 6-methylquinoxaline (60 g, 0.416 mol) in 550 mL of $CCl_4$ was added in one portion solid NBS (Aldrich, 81.5 g, 0.458 mol, 1.1 eq) and AIBN (Aldrich, 1.6 g, 9.7 mmol, 2.3 mol %). The resulting mixture was heated at reflux for 2 hr and cooled to rt. The precipitate of succinimide was removed by filtration. The filtrate was evaporated on rotary evaporator until solid begins to crystallize out of the solution. Remaining mixture was left at rt for 2 hr, then the crystallized product was filtered off, washed with small amount of hexanes-CCl4 mixture (ca. 20:1) and dried in vacuum. The isolated solid contained just traces of the di-bromo side-product and was used in the following step without further purification. Yield 33.3 g (36%) as colorless crystals.

2-(4-tert-butylphenyl)-4-{[4-(6-quinoxalyl)methyl]piperazin-1-yl}benzimidazole

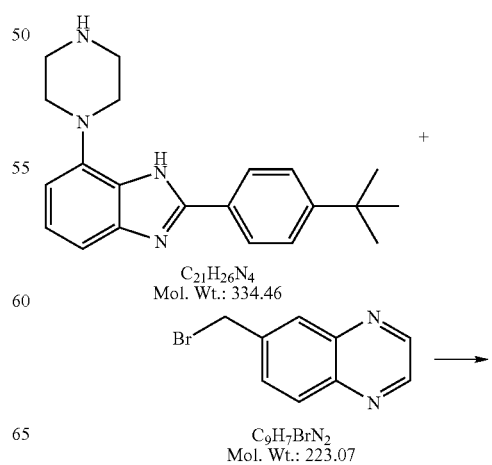

$C_{21}H_{26}N_4$
Mol. Wt.: 334.46

$C_9H_7BrN_2$
Mol. Wt.: 223.07

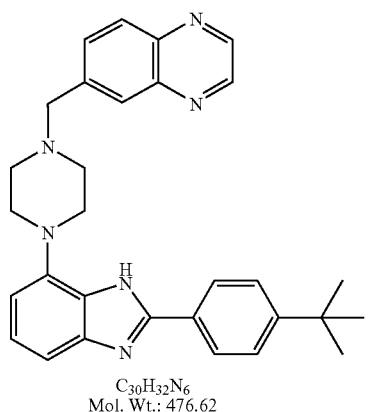

C30H32N6
Mol. Wt.: 476.62

To a suspension of 2-(4-t-butylphenyl)-4-piperazin-1-yl-1H-benzimidazole (49.5 g, 0.148 mol) and potassium carbonate (40.0 g, 0.29 mol) in acetone (0.800 L, EM) was added 6-bromomethylquinoxaline (33.0 g, 0.148 mol) as a solid in one portion at room temperature. The reaction mixture was stirred for 22 h at ambient temperature. The product precipitated out of solution was separated by filtration; the cake was washed with 30 mL of acetone, then triturated with 0.8 L of water and filtered again. The trituration procedure was repeated two more times. The resulting solid was dried in a stream of air first, then in a vacuum desiccator over $CaSO_4$ to give 70 g (0.147 mol) of the desired product as a white amorphous solid. Purity 98% (HPLC at 254 nm).

2-(4-tert-butylphenyl)<sub>4</sub>-{[4-(6-quinoxalyl)methyl]piperazin-1-yl}benzimidazole Dihydrochloride Dihydrate

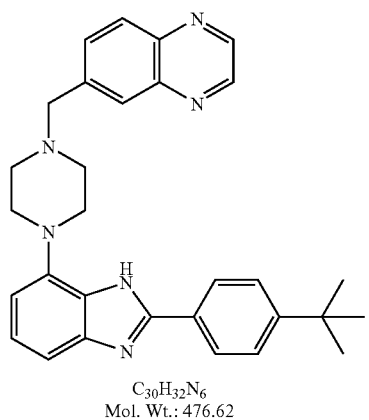

C30H32N6
Mol. Wt.: 476.62

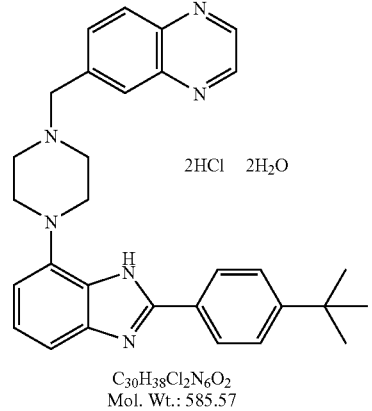

2HCl  2H2O

C30H38Cl2N6O2
Mol. Wt.: 585.57

Removal of Trace Pd

To the suspension of the free base (103 g, 0.216 mol) in EtOAc (1.6 L) was added a solution of L-cysteine (Aldrich, 2.8 g, 23 mmol) in 400 mL of water. The resulting mixture was heated at 50° C. while being stirred rapidly with an overhead stirrer. The mixture became clear when the temperature reached 32° C. After 3 hr of stirring at 50° C., the mixture was allowed to cool to rt. The layers were separated, the aq. layer was extracted with EtOAc (2×50 mL). Combined organic solutions were washed with water, brine, dried over $Na_2SO_4$ and concentrated in vacuum. The residue was triturated with heptane, filtered and dried in a vacuum desiccator to give 102 g (99% recovery) of the product as an off-white solid.

Preparation of the Salt

The free base (110 g, 0.231 mol) was mixed with anhydrous ethanol (0.880 L) and the slurry was heated to 60° C. at which point of the solid dissolved. The resulting clear light-yellow solution was allowed to cool to 40° C., then 2 M solution of HCl in ether (Aldrich, 234 mL, 0.468 mol, 2.03 eq) was added slowly while the solution was being stirred. The resulting mixture remained clear. The stirring was stopped, and the mixture was left overnight at rt. Thick precipitate formed was filtered, washed with 0.6 L of ether and dried in a vacuum oven at 58° C. for 24 hr. Yield of the salt was 105 g (83%).

Various modifications of the invention, in addition to those described herein, will be apparent to those skilled in the art from the foregoing description. Such modifications are also intended to fall within the scope of the appended claims.

What is claimed:

1. A method for preparing a compound having Formula II:

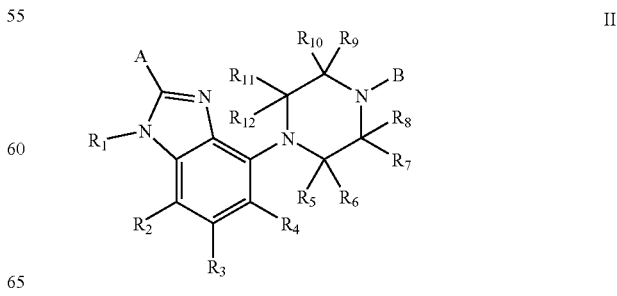

II or a pharmaceutically acceptable salt thereof, wherein

B is $(CR_{13}R_{14})_k$—D,

D is optionally substituted quinoxaline, wherein the substituents are selected from one or more of —V—H, —V-halogen, —V—$N_3$, —V—$NO_2$, —V—CN, —V—OR', —V—SR', —V—$SO_2$R', —V—$SO_2$N(R')$_2$, —V—N(R')$_2$, —V—COR', —V—$CO_2$R', —V—NR'$CO_2$R', —V—NR'COR', —V—NR'CONR', —V—CON(R')$_2$, —C(OH)(CF$_3$)$_2$, —CH(CF$_3$)$_2$, or —C(CF$_3$')$_3$, wherein each R' is independently hydrogen or unsubstituted ($C_1$-$C_6$)-alkyl; and wherein each V is independently a bond or ($C_1$-$C_6$)-alkyl;

k is 0, 1, 2, or 3;

$R_{13}$ and $R_{14}$ are, independently at each occurrence, H or optionally substituted alkyl, wherein the substituents are selected from one or more of —V-halogen, —V—$N_3$, —V—$NO_2$, —V—CN, —V—OR', —V—SR', —V—$SO_2$R', —V—$SO_2$N(R')$_2$, —V—N(R')$_2$, —V—COR', —V—$CO_2$R', —V—NR'$CO_2$R', —V—NR'COR', —V—NR'CONR', —V—CON(R')$_2$, —C(OH)(CF$_3$)$_2$, —CH(CF)$_2$, or —C(CF$_3$)$_3$, wherein each R' is independently hydrogen or unsubstituted ($C_1$-$C_6$)-alkyl; and wherein each V is independently a bond or ($C_1$-$C_6$)-alkyl, A is optionally substituted phenyl, wherein the substituents are selected from one or more of —V—H, —V-halogen, —V—$N_3$, —V—$NO_2$, —V—CN, —V—OR', —V—SR', —V—$SO_2$R', —V—$SO_2$N(R')$_2$, —V—N(R')$_2$, —V—COR', —V—$CO_2$R', —V—NR'$CO_2$R', —V—NR'COR', —V—NR'CONR', —V—CON(R')$_2$, —C(OH)(CF$_3$)$_2$, —CH(CF$_3$)$_2$, or —C(CF$_3$)$_3$, wherein each R' is independently hydrogen or unsubstituted ($C_1$-$C_6$)-alkyl; and wherein each V is independently a bond or ($C_1$-$C_6$)-alkyl, $C_1$-$C_6$ alkyl, $C_1$-$C_6$ alkenyl, $C_2$-$C_6$ alkynyl, $NR_{22}R_{23}$, $CR_{24}(CF_3)_2$, $JR_{22}$, or $C(=O)R_{22}$, wherein J is O or $SO_m$, wherein m is 0, 1, or 2;

$R_{22}$ and $R_{23}$ are, independently, H, $C_1$-$C_7$ alkyl, $C_2$-$C_7$ alkenyl, $C_2$-$C_7$ alkynyl, aryl, or heteroalkyl, each alkyl, alkenyl, alkynyl, aryl, or heteroalkyl being optionally substituted, alternatively, $R_{22}$ and $R_{23}$, taken together with the atoms to which they are attached, form an optionally substituted cyclic or optionally substituted heterocyclic group, having from 3-8 ring members and the heteroatoms are selected from O, N and S, optionally substituted with $R_{20}$—E—$R_{21}$, wherein E is O, N, $NR_{21}$, or $SO_m$, $R_{20}$ and $R_{21}$ are, independently, H, $C_1$-$C_3$ alkyl, or heteroalkyl, alternatively, $R_{20}$ and $R_{21}$, taken together with the atoms to which they are attached, form a cyclic or heterocyclic group, having from 3-8 ring members and the heteroatoms are selected from O, N and S; and $R_{24}$ is H, or OH;

$R_2$, $R_3$, and $R_4$ are H; and $R_1$, $R_5$, $R_6$, $R_7$, $R_8$, $R_9$, $R_{10}$, $R_{11}$, and $R_{12}$, are, independently, H or optionally substituted alkyl, wherein the substituents are selected from one or more of —V-halogen, —V—$N_3$, —V—$NO_2$, —V—CN, —V—OR', —V—SR', —V—$SO_2$R', —V—$SO_2$N(R')$_2$, —V—N(R')$_2$, —V—COR', —V—$CO_2$R', —V—NR'$CO_2$R', —V—NR'COR', —V—NR'CONR', —V—CON(R')$_2$, —C(OH)(CF$_3$)$_2$, —CH(CF$_3$)$_2$, or —C(CF$_3$)$_3$, wherein each R' is independently hydrogen or unsubstituted ($C_1$-$C_6$)-alkyl; and wherein each V is independently a bond or ($C_1$-$C_6$)-alkyl;

which comprises reacting a compound having Formula I:

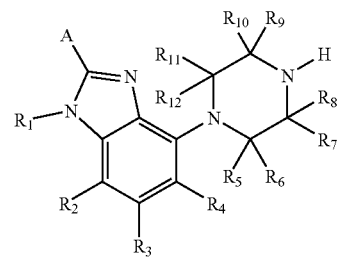

wherein A and $R_1$-$R_{12}$ are as defined above;
with a compound having formula:

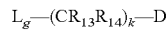

wherein D, k and $R_{13}$ and $R_{14}$ are as defined above, and $L_g$ is halogen or $OSO_2R_{32}$, wherein $R_{32}$ is an optionally substituted alkyl, wherein the substitutents are selected from one or more of —V-halogen, —V—$N_3$, —V—$NO_2$, —V—CN, —V—OR', —V—SR', —V—$SO_2$R', —V—$SO_2$N(R')$_2$, —V—N(R')$_2$, —V—COR', —V—$CO_2$R', —V—NR'$CO_2$R', —V—NR'COR', —V—NR'CONR', —V—CON(R')$_2$, —C(OH)(CF$_3$)$_2$, —CH(CF$_3$)$_2$, or —C(CF$_3$)$_3$, wherein each R' is independently hydrogen or unsubstituted ($C_1$-$C_6$)-alkyl; and wherein each V is independently a bond or ($C_1$-$C_6$)-alkyl, or an optionally substituted aryl, wherein the substituents are selected from one or more of —V—H, —V-halogen, —V—$N_3$, —V—$NO_2$, —V—CN, —V—OR', —V—SR', —V—$SO_2$R', —V—$SO_2$N(R')$_2$, —V—N(R')$_2$, —V—COR', —V—$CO_2$R', —V—NR'$CO_2$R', —V—NR'COR', —V—NR'CONR', —V—CON(R')$_2$, —C(OH)(CF$_3$)$_2$, —CH(CF$_3$)$_2$, or —C(CF$_3$)$_3$, wherein each R' is independently hydrogen or unsubstituted ($C_1$-$C_6$)-alkyl; and wherein each V is independently a bond or ($C_1$-$C_6$)-alkyl, $C_2$-$C_6$ alkenyl, $C_2$-$C_6$ alkynyl, $NR_{22}R_{23}$, $CR_{24}(CF_3)_2$, $JR_{22}$, or $C(=O)R_{22}$, wherein J is O or $SO_m$, wherein m is 0, 1, or 2; $R_{22}$ and $R_{23}$ are, independently, H, $C_1$-$C_7$ alkyl, $C_2$-$C_7$ alkenyl, $C_2$-$C_7$ alkynyl, aryl, or heteroalkyl, each alkyl, alkenyl, alkynyl, aryl, or heteroaryl being optionally substituted, alternatively, $R_{22}$ and $R_{23}$, taken together with the atoms to which they are attached, form an optionally substituted cyclic or optionally substituted heterocyclic group, having from 3-8 ring members and the heteroatoms are selected from O, N and S optionally substituted with $R_{20}$—E—$R_{21}$, wherein E is O, N, $NR_{21}$, or $SO_m$, $R_{20}$ and $R_{21}$ are, independently, H, $C_1$-$C_3$ alkyl, or heteroalkyl, alternatively, $R_{20}$ and $R_{21}$, taken together with the atoms to which they are attached, form a cyclic or heterocyclic group, having from 3-8 ring members and the heteroatoms are selected from O, N and S; and $R_{24}$ is H, or OH, or an optionally substituted fluoroalkyl, wherein the substituents are selected from one or more of $C_1$-$C_6$ alkyl including straight and branched chain aliphatic groups having from 1 to 6 carbons;

in an organic solvent in the presence of a base; and optionally converting the compound of Formula II to a pharmaceutically acceptable salt.

2. The method of claim 1, wherein $R_1$ is H or $C_1$-$C_3$ alkyl.

3. The method of claim 1, wherein $R_5$, $R_6$, $R_7$, $R_8$, $R_9$, $R_{10}$, $R_{11}$ and $R_{12}$, are, independently, H or $C_1$-$C_4$ alkyl.

4. The method of claim 1, wherein the compound of Formula I has the formula:

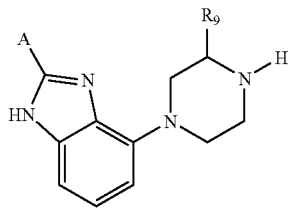

wherein A is optionally substituted phenyl and $R_9$ is H or $C_1$-$C_4$ alkyl.

5. The method of claim 4, wherein the compound of Formula I is prepared by a process comprising reacting a compound having formula

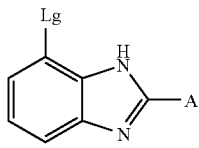

V with a compound having formula

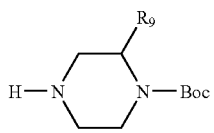

VI wherein $L_g$ is as defined in claim 1, and $R_9$ is as defined in claim 4, and Boc is tertiary butyloxycarbonyl, and removing the Boc protecting group.

6. The method of claim 5, wherein $L_g$ is Br or triflate.

7. The method of claim 5, wherein the reaction of the compounds of Formula V and VI is carried Out in toluene-THF in the presence of $Pd_2(dba)_3$ and CyMAP ligand with solid lithium hexamethyldisilazide.

8. The method of claim 5, wherein the compound of formula

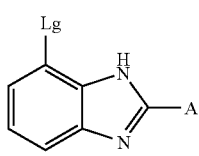

V is prepared by a process comprising chlorinating a compound having formula

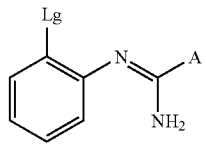

with N-chlorosuccinimide in methanol, and reacting the resulting N-chloride with potassium carbonate.

9. The method of claim 8, wherein the compound having formula

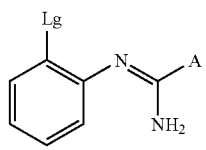

is prepared by a process comprising reacting a compound having formula

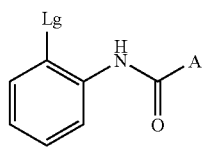

with thionyl chloride to form an imidoyl chloride, and reacting said imidoyl chloride with aqueous ammonia.

10. The method of claim 9, wherein the compound having formula

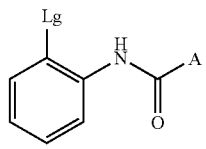

is prepared by a process comprising reacting a compound of formula

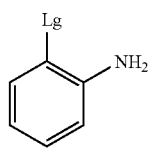

with a compound of formula

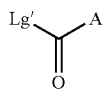

wherein $L_g'$ is a halogen.

11. The method of claim 10, wherein Lg' is Br.

12. The method of claim 10, wherein the reaction of the compounds of formula

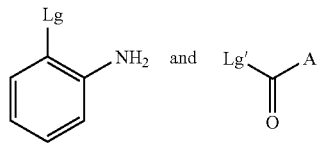

is carried out under Schotten-Bauman conditions with NaHCO$_3$.

13. The method of claim 1, wherein R$_{13}$ and R$_{14}$ are, independently at each occurrence, H or C$_1$-C$_3$ alkyl.

14. The method of claim 1, wherein A is phenyl substituted with C$_1$-C$_6$ alkyl, C$_2$-C$_6$ alkenyl, C$_2$-C$_6$ alkynyl, NR$_{22}$R$_{23}$, CR$_{24}$(CF$_3$)$_2$, JR$_{22}$, or C(=O)R$_{22}$, wherein J is O or SO$_m$, wherein m is 0, 1, or 2;

R$_{22}$ and R$_{23}$ are, independently, H, C$_1$-C$_7$ alkyl, C$_2$-C$_7$ alkenyl, C$_2$-C$_7$ alkynyl, aryl, or heteroalkyl, wherein each alkyl, alkenyl, alkynyl, or heteroalkyl may be optionally substituted, wherein the substituents are selected from one or more of —V-halogen, —V—N$_3$, —V—NO$_2$, —V—CN, —V—OR', —V—SR', —V—SO$_2$R', —V—SO$_2$N(R')$_2$, —V—N(R')$_2$, —V—COR', —V—CO$_2$R', —V—NR'CO$_2$R', —V—NR'COR', —V—NR'CONR', —V—CON(R')$_2$, —C(OH)(CF$_3$)$_2$, —CH(CF$_3$)$_2$, or —C(CF$_3$)$_3$, wherein each R' is independently hydrogen or unsubstituted (C$_1$-C$_6$)-alkyl; and wherein each V is independently a bond or (C$_1$-C$_6$)-alkyl, or each aryl may be optionally substituted, wherein the substitutents are selected from one or more of —V—H, —V-halogen, —V—N$_3$, —V—NO$_2$, —V—CN, —V—OR', —V—SR', —V—SO$_2$R', —V—SO$_2$N (R')$_2$, —V—N(R')$_2$, —V—COR', —V—CO$_2$R', —V—NR'CO$_2$R', —V—NR'COR', —V—NR'CONR', —V—CON(R')$_2$, —C(OH)(CF$_3$)$_2$, —CH(CF$_3$)$_2$, or —C(CF$_3$)$_3$, wherein each R' is independently hydrogen or unsubstituted (C$_1$-C$_6$)-alkyl; and wherein each V is independently a bond or (C$_1$-C$_6$)-alkyl, C$_2$-C$_6$ alkenyl, C$_2$-C$_6$ alkynyl, NR$_{22}$R$_{23}$, CR$_{24}$(CF$_3$)$_2$, JR$_{22}$, or C(=O) R$_{22}$, wherein J is O or SO$_m$, wherein m is 0, 1, or 2;

R$_{22}$ and R$_{23}$ are, independently, H, C$_1$-C$_7$ alkyl, C$_2$-C$_7$ alkenyl, C$_1$-C$_7$ alkynyl, aryl, or heteroalkyl, each alkyl, alkenyl, alkynyl, aryl, or heteroaryl being optionally substituted, alternatively, R$_{22}$ and R$_{23}$, taken together with the atoms to which they are attached, form an optionally substituted cyclic or optionally substituted heterocyclic group, having from 3-8 ring members and the heteroatoms are selected from O, N and S optionally substituted with R$_{20}$—E—R$_{21}$, wherein E is O, N, NR$_{21}$, or SO$_m$, R$_{20}$ and R$_{21}$ are, independently, H, C$_1$-C$_3$ alkyl, or heteroalkyl, alternatively, R$_{20}$ and R$_{21}$, taken together with the atoms to which they are attached, form a cyclic or heterocyclic group, having from 3-8 ring members and the heteroatoms are selected from O, N and S; and R$_{24}$ is H, or OH, alternatively, R$_{22}$ and R$_{23}$, taken together with the atoms to which they are attached, form an optionally substituted cyclic or optionally substituted heterocyclic group optionally substituted with R$_{20}$—E—R$_{21}$, wherein E is O, N, NR$_{21}$, or SO$_m$, R$_{20}$ and R$_{21}$ are, independently, H, C$_1$-C$_3$ alkyl, or heteroalkyl, alternatively, R$_{20}$ and R$_{21}$, taken together with the atoms to which they are attached, form a cyclic or heterocyclic group; and R$_{24}$ is H, or OH.

15. The method of claim 1, wherein A is para t-butyl phenyl.

16. The method of claim 1, wherein D is (quinoxalin-6-yl) methyl.

17. The method of claim 1, wherein L$_g$ is Br.

18. The method of claim 1, wherein L$_g$—(CR$_{13}$R$_{14}$)$_k$—D is 6-bromomethyl-quinoxaline.

19. The method of claim 18, wherein the 6-bromomethyl-quinoxaline is prepared by a process comprising brominating 6-methylquinoxaline.

20. The method of claim 18, wherein the bromination is achieved using N-bromosuccinimide and azobisisobutyronitrile in carbon tetrachloride at reflux.

21. The method of claim 19, wherein the 6-methylquinoxaline is prepared by a process comprising reacting 4-methylphenylene-1,2-diamine with glyoxal.

22. The method of claim 1, wherein the organic solvent comprises at least one of acetone, acetonitrile, dimethylsulfoxide, and tetrahydrofuran.

23. The method of claim 1, wherein the base comprises potassium carbonate or N,N-diisopropylethylamine.

24. The method of claim 1, wherein the base comprises potassium carbonate and the organic solvent comprises acetone.

25. The method of claim 23, wherein 2 equivalents of potassium carbonate are used.

26. The method of claim 1, wherein 1 equivalent of L$_g$—(CR$_{13}$R$_{14}$)$_k$—D is used.

27. A method for preparing a compound of Formula IV:

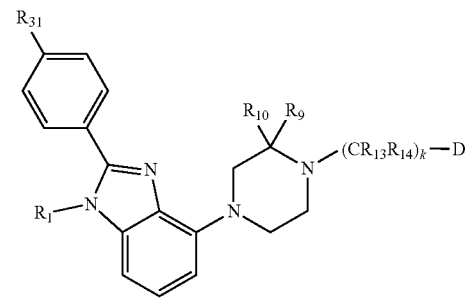

IV or a pharmaceutically acceptable salt thereof
wherein

R$_1$ is H or alkyl;

R$_9$ and R$_{10}$, are, independently, H or optionally substituted alkyl, wherein the substituents are selected from one or more of —V-halogen, —V—N$_3$, —V—NO$_2$, —V—CN, —V—OR', —V—SR', —V—SO—R', —V—SO$_2$N(R')$_2$, —V—N(R')$_2$, —V—COR', —V—CO$_2$R', —V—NR'CO$_2$R', —V—NR'COR', —V—NR'CONR', —V—CON(R')$_2$, —C(OH)(CF$_3$)$_2$, —CH(CF$_3$)$_2$, or —C(CF$_3$)$_3$, wherein each R' is independently hydrogen or unsubstituted (C$_1$-C$_6$)-alkyl; and wherein each V is independently a bond or (C$_1$-C$_6$)-alkyl; and R$_{31}$ is C$_1$-C$_6$ alkyl, C$_2$-C$_6$ alkenyl, C$_2$-C$_6$ alkynyl, NR$_{22}$R$_{23}$, CR$_{24}$(CF$_3$)$_2$, JR$_{22}$, or C(=O)R$_{22}$, wherein J is O or SO$_m$, wherein m is 0, 1, or 2;

$R_{22}$ and $R_{23}$ are, independently, H, $C_1$-$C_7$ alkyl, $C_2$-$C_7$ alkenyl, $C_2$-$C_7$ alkynyl, aryl, or heteroalkyl, each alkyl, alkenyl, alkynyl, or heteroalkyl may be optionally substituted, wherein the substitutents are selected from one or more of —V-halogen, —V—N3, —V—NO$_2$, —V—CN, —V—OR', —V—SR', —V—SO$_2$R', —V—SO$_2$N(R')$_2$, —V—N(R')$_2$, —V—COR', —V—CO$_2$R', —V—NR'CO$_2$R', —V—NR'COR', —V—NR'CONR', V—CON(R')$_2$, —C(OH)(CF$_3$)$_2$, —CH(CF$_3$)$_2$, or —C(CF$_3$)$_3$, wherein each R' is independently hydrogen or unsubstituted ($C_1$-$C_6$)-alkyl; and wherein each V is independently a bond or ($C_1$-$C_6$)-alkyl, or each aryl may be optionally substituted, wherein the substitutents are selected from one or more of —V—H, —V-halogen, —V—N$_2$, —V—NO$_2$, —V—CN, —V—OR', —V—SR', —V—SO$_2$R', —V—SO$_2$N(R')$_2$, —V—N(R')$_2$, —V—COR', —V—CO$_2$R', —V—NR'CO$_2$R', —V—NR'COR', —V—NR'CONR', —V—CON(R')$_2$, —C(OH)(CF$_3$)$_2$, —CH(CF$_3$)$_2$, or —C(CF$_3$)$_3$, wherein each R' is independently hydrogen or unsubstituted ($C_1$-$C_6$)-alkyl; and wherein each V is independently a bond or ($C_1$-$C_6$)-alkyl, $C_2$-$C_6$ alkenyl, $C_2$-$C_6$ alkynyl, NR$_{22}$R$_{23}$, CR$_{24}$(CF$_3$)$_2$, JR$_{22}$, or C(═O)R$_{22}$, wherein J is O or SO$_m$, wherein m is 0, 1, or 2;

$R_{22}$ and $R_{23}$ are, independently, H, $C_1$-$C_7$ alkyl, $C_2$-$C_7$ alkenyl, $C_2$-$C_7$ alkynyl, aryl, or heteroalkyl, each alkyl, alkenyl, alkynyl, aryl, or heteroaryl being optionally substituted, alternatively, $R_{22}$ and $R_{23}$, taken together with the atoms to which they are attached, form an optionally substituted cyclic or optionally substituted heterocyclic group, having from 3-8 ring members and the heteroatoms are selected from O, N and S optionally substituted with R$_{20}$—E—R$_{21}$, wherein E is O, N, NR$_{21}$, or SO$_m$, R$_{20}$ and R$_{21}$ are, independently, H, $C_1$-$C_3$ alkyl, or heteroalkyl, alternatively, $R_{20}$ and $R_{21}$, taken together with the atoms to which they are attached, form a cyclic or heterocyclic group, having from 3-8 ring members and the heteroatoms are selected from O, N and S; and alternatively, $R_{22}$ and $R_{23}$, taken together with the atoms to which they are attached, form a cyclic or heterocyclic group optionally substituted with R$_{20}$—E—R$_{21}$, wherein E is O, N, NR$_{21}$, or SO$_m$, $R_{20}$ and $R_{21}$ are, independently, H, $C_1$-$C_3$ alkyl, or heteroalkyl, alternatively, $R_{20}$ and $R_{21}$, taken together with the atoms to which they are attached, form a cyclic or heterocyclic group; and $R_{24}$ is H, or OH;

D is optionally substituted quinoxaline, wherein the substitutents are selected from one or more of —V—H, —V-halogen, —V—N$_3$, —V—NO$_2$, —V—CN, —V—OR', —V—SR', —V—SO$_2$R', —V—SO$_2$N(R')$_2$, —V—N(R')$_2$, —V—COR', —V—CO$_2$R', —V—NR'CO$_2$R', —V—NR'COR', —V—NR'CONR', —V—CON(R')$_2$, —C(OH)(CF$_3$)$_2$, —CH(CF$_3$)$_2$, or —C(CF$_3$)$_3$, wherein each R' is independently hydrogen or unsubstituted ($C_1$-$C_6$)-alkyl; and wherein each V is independently a bond or ($C_1$-$C_6$)-alkyl;

$L_g$ is halogen or OSO$_2$R$_{32}$, wherein R$_{32}$ is alkyl, or fluoroalkyl, that may be optionally substituted, wherein the substitutents are selected from one or more of —V-halogen, —V—N$_3$, —V—NO$_2$, —V—CN, —V—OR', —V—SR', —V—SO$_2$R', —V—SO$_2$N(R')$_2$, —V—N(R')$_2$, —V—COR', —V—CO$_2$R', —V—NR'CO$_2$R', —V—NR'COR', —V—NR'CONR', —V—CON(R')$_2$, —C(OH)(CF$_3$)$_2$, —CH(CF$_3$)$_2$, or —C(CF$_3$)$_3$, wherein each R' is independently hydrogen or unsubstituted ($C_1$-$C_6$)-alkyl; and wherein each V is independently a bond or ($C_1$-$C_6$)-alkyl, or aryl that may be optionally substituted, wherein the substitutents are selected from one or more of —V—H, —V-halogen, —V—N$_3$, —V—NO$_2$, —V—CN, —V—OR', —V—SR', —V—SO$_2$R', —V—SO$_2$N(R')$_2$, —V—N(R')$_2$, —V—COR', —V—CO$_2$R', —V—NR'CO$_2$R', —V—NR'COR', —V—NR'CONR', —V—CON(R')$_2$, —C(OH)(CF$_3$)$_2$, —CH(CF$_3$)$_2$, or —C(CF$_3$)$_3$, wherein each R' is independently hydrogen or unsubstituted ($C_1$-$C_6$)-alkyl; and wherein each V is independently a bond or ($C_1$-$C_6$)-alkyl, $C_1$-$C_6$ alkyl, $C_2$-$C_6$ alkenyl, $C_2$-$C_6$ alkynyl, NR$_{22}$R$_{23}$, CR$_{24}$(CF$_3$)$_2$, JR$_{22}$, or C(═O)R$_{22}$, wherein J is O or SO$_m$, wherein m is 0, 1, or 2;

$R_{22}$ and $R_{23}$ are, independently, H, $C_1$-$C_7$ alkyl, $C_2$-$C_7$ alkenyl, $C_2$-$C_7$ alkynyl, aryl, or heteroalkyl, each alkyl, alkenyl, alkynyl, aryl, or heteroaryl being optionally substituted, alternatively, $R_{22}$ and $R_{23}$, taken together with the atoms to which they are attached, form an optionally substituted cyclic or optionally substituted heterocyclic group, having from 3-8 ring members and the heteroatoms are selected from O, N and S optionally substituted with R$_{20}$—E—R$_{21}$, wherein E is O, N, NR$_{21}$, or SO$_m$, R$_{20}$ and R$_{21}$ are, independently, H, $C_1$-$C_3$ alkyl, or heteroalkyl, alternatively, $R_{20}$ and $R_{21}$, taken together with the atoms to which they are attached, form a cyclic or heterocyclic group, having from 3-8 ring members and the heteroatoms are selected from O, N and S; and $R_{24}$ is H, or OH;

k is 0, 1, 2, or 3; and $R_{13}$ and $R_{14}$ are, independently at each occurrence, H or optionally substituted alkyl, wherein the substitutents are selected from one or more of —V-halogen, —V—N$_3$, —V—NO, —V—CN, —V—OR', —V—SR', —V—SO$_2$R', —V—SO$_2$N(R')$_2$, —V—N(R')$_2$, —V—COR', —V—CO$_2$R', —V—NR'CO$_2$R', —V—NR'COR', —V—NR'CONR', —V—CON(R')$_2$, —C(OH)(CF$_3$)$_2$, —CH(CF$_3$)$_2$, or —C(CF$_3$')$_3$, wherein each R' is independently hydrogen or unsubstituted ($C_1$-$C_6$)-alkyl; and wherein each V is independently a bond or ($C_1$-$C_6$)-alkyl, and which comprises reacting a compound having Formula III:

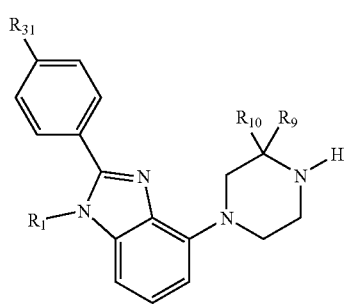

III with a compound having formula:

wherein $L_g$, $R_{13}$, $R_{14}$, k and D are as defined above, in an organic solvent in the presence of base; and optionally converting the compound of Formula IV to a pharmaceutically acceptable salt.

28. The method of claim 27, wherein $R_1$ is H or O, $C_1$-$C_3$ alkyl.

29. The method of claim 27, wherein $R_9$ and $R_{10}$, are, independently, H or $C_1$-$C_4$ alkyl.

30. The method of claim 27, wherein $R_{13}$ and $R_{14}$ are, independently at each occurrence, H or $C_1$-$C_3$ alkyl.

31. The method of claim 27, wherein $L_g$—$(CR_{13}R_{14})_k$—D is 6-bromomethyl-quinoxaline.

32. The method of claim 27, wherein $L_g$ is Br.

33. The method of claim 31, wherein the 6-bromomethyl-quinoxaline is prepared by a process which comprises brominating 6-methylquinoxaline.

34. The method of claim 33, wherein the bromination is achieved using N-bromosuccinimide and azobisisobutyronitrile in carbon tetrachloride at reflux.

35. The method of claim 33, wherein 6-methylquinoxaline is prepared by a process which comprises reacting 4-methylphenylene-1,2-di amine with glyoxal.

36. The method of claim 27, wherein the base comprises potassium carbonate and N,N-diisopropylethyl amine.

37. The method of claim 27, wherein the organic solvent comprises at least one of acetone, acetonitrile, dimethylsulfoxide, and tetrahydrofuran.

38. The method of claim 27, wherein the base comprises potassium carbonate and the organic solvent comprises acetone.

39. The method of claim 36, wherein 2 equivalents of potassium carbonate are used.

40. The method of claim 27, wherein 1 equivalent of $L_g$—$(CR_{13}R_{14})_k$—D is used.

41. The method of claim 27, wherein the compound of Formula III is prepared by a process which comprises reacting a compound having formula

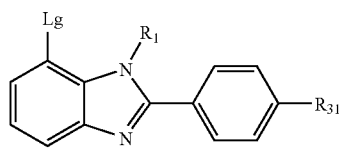

with a compound having formula

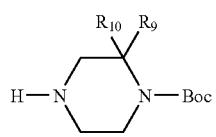

and deprotecting.

42. The method of claim 41, wherein $L_g$ is Br.

43. The method of claim 41, wherein the reaction is carried out in toluene-THF in the presence of $Pd_2(dba)_3$ and CyMAP ligand with solid lithium hexamethyldisilazide.

44. The method of claim 41, wherein the compound having formula

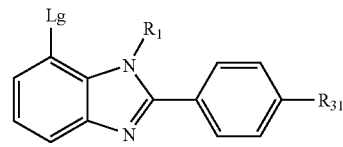

is prepared by a process which comprises chlorinating a compound having formula

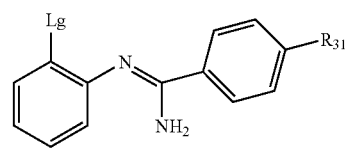

with N-chlorosuccinimide in methanol, and reacting the resulting N-chloride with potassium carbonate.

45. The method of claim 44, wherein the compound having formula

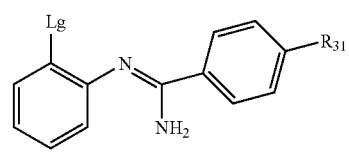

is prepared by a process which comprises reacting a compound having formula

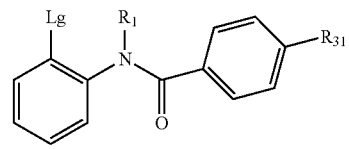

with thionyl chloride to form an imidoyl chloride, and reacting the imidoyl chloride with aqueous ammonia.

46. The method of claim 45, wherein the compound having formula

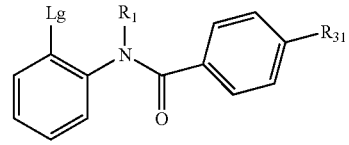

is prepared by a process which comprises reacting a compound of formula

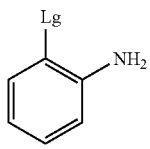

with a compound of formula

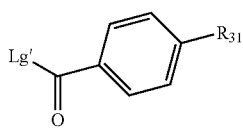

wherein $L_g$ is a halogen.

47. The method of claim 46, wherein

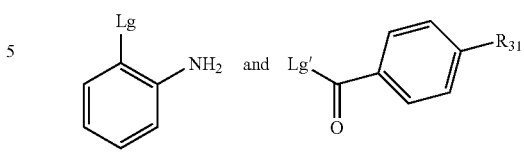

are combined under Schotten-Bauman conditions with $NaHCO_3$.

48. The method of claim 46, wherein $L_g'$ is Br.

49. The method of claim 27, wherein $R_{31}$ is t-butyl.

50. The method of claim 1, wherein the compound of Formula II is converted to a salt by a process comprising adding 2 equivalents of ethereal HCl to a solution of the compound having Formula II in ethanol.

51. The method of claim 27, wherein the compound of Formula IV is converted to a salt by a process comprising adding 2 equivalents of ethereal HCl to a solution of the compound having Formula IV in ethanol.

* * * * *